(12) United States Patent
Vann et al.

(10) Patent No.: US 6,887,431 B1
(45) Date of Patent: May 3, 2005

(54) BEAD DISPENSING SYSTEM

(75) Inventors: Charles S. Vann, Burlingame, CA (US); Dennis Lehto, Santa Clara, CA (US)

(73) Assignees: Applera Corporation, Foster City, CA (US); Applied Biosystems Group

( * ) Notice: Subject to any disclaimer, the term of this patent is extended or adjusted under 35 U.S.C. 154(b) by 0 days.

(21) Appl. No.: 09/506,870

(22) Filed: Feb. 15, 2000

Related U.S. Application Data

(63) Continuation-in-part of application No. 09/250,697, filed on Feb. 16, 1999, now abandoned.

(51) Int. Cl.[7] .......................... B01L 3/02; G01N 21/00; G01N 33/545; C12M 1/34; B65G 59/00
(52) U.S. Cl. .......................... 422/100; 422/63; 422/99; 436/528; 436/531; 436/532; 436/43; 436/178; 435/288.4; 435/288.7; 221/264
(58) Field of Search .......................... 422/68.1, 63–65, 422/81, 99–100, 102, 131; 430/528, 531–532, 43, 49, 54, 177–178, 801; 435/257.2–257.3, 288.4–288.7; 221/264, 95

(56) References Cited

U.S. PATENT DOCUMENTS

| | | | |
|---|---|---|---|
| 4,101,284 A | | 7/1978 | Difiglio et al. |
| 4,236,825 A | * | 12/1980 | Gilford et al. ............... 356/414 |
| 4,272,510 A | | 6/1981 | Smith et al. .................. 427/47 |
| 4,415,098 A | | 11/1983 | Haas |
| 4,593,728 A | | 6/1986 | Whitehead et al. |
| 4,648,529 A | | 3/1987 | Blakemore et al. |
| 4,649,116 A | * | 3/1987 | Daty et al. ............... 435/287.2 |
| 4,681,742 A | | 7/1987 | Johnson et al. |
| 4,685,480 A | * | 8/1987 | Eck ............................. 134/182 |
| 4,699,884 A | | 10/1987 | Noss et al. |

(Continued)

FOREIGN PATENT DOCUMENTS

| | | |
|---|---|---|
| DE | 197 12 195 | 9/1998 |
| EP | 0 955 084 | 11/1999 |
| JP | 01080862 | 3/1989 |
| WO | WO 97/38318 | 10/1997 |
| WO | 97/40383 | 10/1997 |

(Continued)

OTHER PUBLICATIONS

Brussolo, J.S., and Dewitt, S.H., "Automated Sample Handling Systems," *NetSci Articles* 1(5):1–10 (1995).

(Continued)

*Primary Examiner*—Jill Warden
*Assistant Examiner*—Brian R. Gordon
(74) *Attorney, Agent, or Firm*—Woodcock Washburn LLP

(57) ABSTRACT

A bead dispensing system is provided for delivering small amounts of substances onto substrates. The system can include, for example, a movable support structure having an array of spaced-apart projections depending from its lower side. An attraction source, such as a vacuum, magnetic, and/or electrostatic force, is operable at each projection end region to attract and retain one bead. The projection array can be aligned with an array of bead-receiving regions of a substrate, e.g., an array of spaced-apart wells of a microplate or card. In one embodiment, a plurality of reagent-carrying beads are picked up, retained at respective projection end regions, and moved to a location over a multi-well plate. The beads are then released in a fashion permitting each bead to land in a respective well. The system of the invention is particularly useful for fabricating arrays of reagents.

34 Claims, 20 Drawing Sheets

U.S. PATENT DOCUMENTS

| | | | |
|---|---|---|---|
| 4,770,454 A | * | 9/1988 | Muscher et al. ............ 294/64.1 |
| 4,887,351 A | * | 12/1989 | Porterfield et al. ............ 29/740 |
| 4,937,048 A | | 6/1990 | Sakai et al. |
| 4,952,518 A | | 8/1990 | Johnson et al. |
| 5,011,779 A | | 4/1991 | Maimon |
| 5,048,226 A | | 9/1991 | Hamilton |
| 5,185,269 A | * | 2/1993 | Wells ........................ 436/180 |
| 5,255,618 A | | 10/1993 | Berry |
| 5,382,512 A | | 1/1995 | Smethers et al. |
| 5,409,347 A | | 4/1995 | Suzuki |
| 5,445,934 A | | 8/1995 | Fodor et al. |
| 5,447,736 A | | 9/1995 | Gorlich ...................... 426/396 |
| 5,467,913 A | | 11/1995 | Namekawa et al. |
| 5,508,200 A | | 4/1996 | Tiffany et al. |
| 5,514,785 A | | 5/1996 | Van Ness et al. |
| 5,518,883 A | | 5/1996 | Soini |
| 5,567,326 A | | 10/1996 | Ekenberg et al. ........... 210/695 |
| 5,571,258 A | | 11/1996 | Pearson |
| 5,601,229 A | | 2/1997 | Nakazato et al. |
| 5,616,299 A | | 4/1997 | Walker et al. |
| 5,649,576 A | | 7/1997 | Kirk et al. .................. 141/129 |
| 5,677,195 A | | 10/1997 | Winkler et al. |
| 5,722,470 A | | 3/1998 | Kedar et al. |
| 5,756,050 A | | 5/1998 | Ershow et al. |
| 5,763,263 A | | 6/1998 | Dehlinger |
| 5,770,860 A | | 6/1998 | Franzen |
| 5,772,966 A | | 6/1998 | Maracas et al. |
| 5,773,296 A | | 6/1998 | Montalbano et al. |
| 5,788,814 A | | 8/1998 | Sun et al. |
| 5,846,595 A | | 12/1998 | Sun et al. |
| 5,849,598 A | | 12/1998 | Wilson et al. ............... 436/180 |
| 5,935,859 A | * | 8/1999 | Elliott et al. .................. 436/54 |
| 5,979,251 A | | 11/1999 | James et al. ............. 73/963.02 |
| 6,074,609 A | * | 6/2000 | Gavin et al. ................... 422/99 |
| 6,187,270 B1 | * | 2/2001 | Schmitt et al. ............. 422/101 |
| 6,288,220 B1 | * | 9/2001 | Kambara et al. ........... 204/406 |
| 6,387,331 B1 | | 5/2002 | Hunter ....................... 422/102 |
| 6,471,917 B1 | * | 10/2002 | Velkovska et al. .......... 422/100 |
| 2002/0015666 A1 | * | 2/2002 | Vann et al. .................. 422/100 |
| 2003/0166299 A1 | * | 9/2003 | Velkovska et al. .......... 436/180 |

FOREIGN PATENT DOCUMENTS

| | | |
|---|---|---|
| WO | 97/44134 | 11/1997 |
| WO | 98/08092 | 2/1998 |
| WO | 98/17383 | 4/1998 |
| WO | WO 98/20019 | 5/1998 |
| WO | WO 98/32000 | 7/1998 |
| WO | 98/38122 | 9/1998 |

OTHER PUBLICATIONS

Castellino, A.M., "When the Chips are Down," *Genome Research* 7:943–946 (1997).

Editorial, "Getting hip to the chip," *Nature Genetics* 18(3):195–197 (1998).

Fodor, S.P.A., et al., "Light–directed Spatially Addressable Parallel Chemical Synthesis," *Science* 251: 767–773 (1991).

Haystack™ brochure, The Automation Partnership, First Edition: Oct. 1995.

Lemmo, A.V., et al., "Characterization of an Inkjet Chemical Microdispenser for Combinatorial Library Synthesis," *Analytical Chemistry* 69(4):543–551 (1997).

* cited by examiner

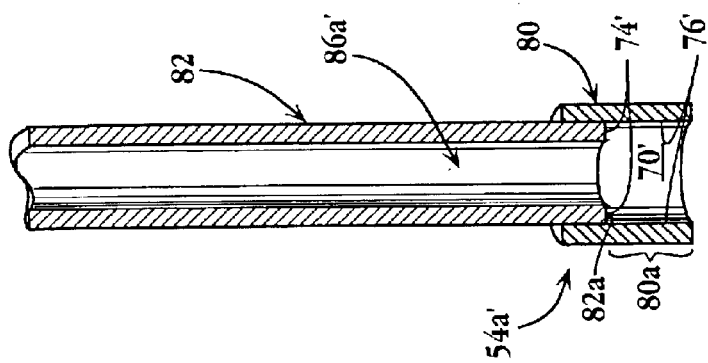
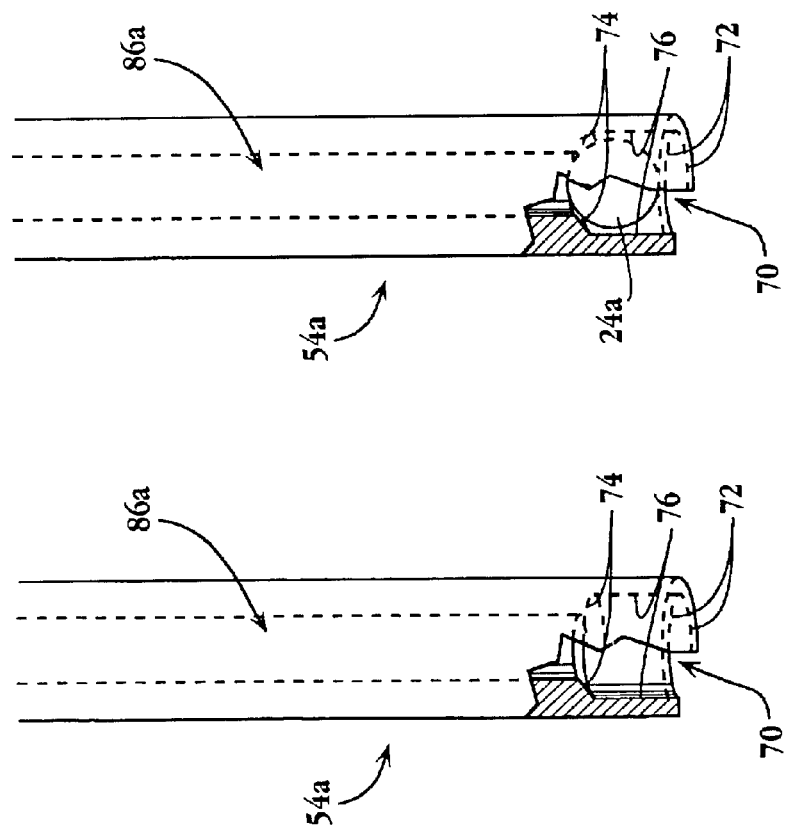

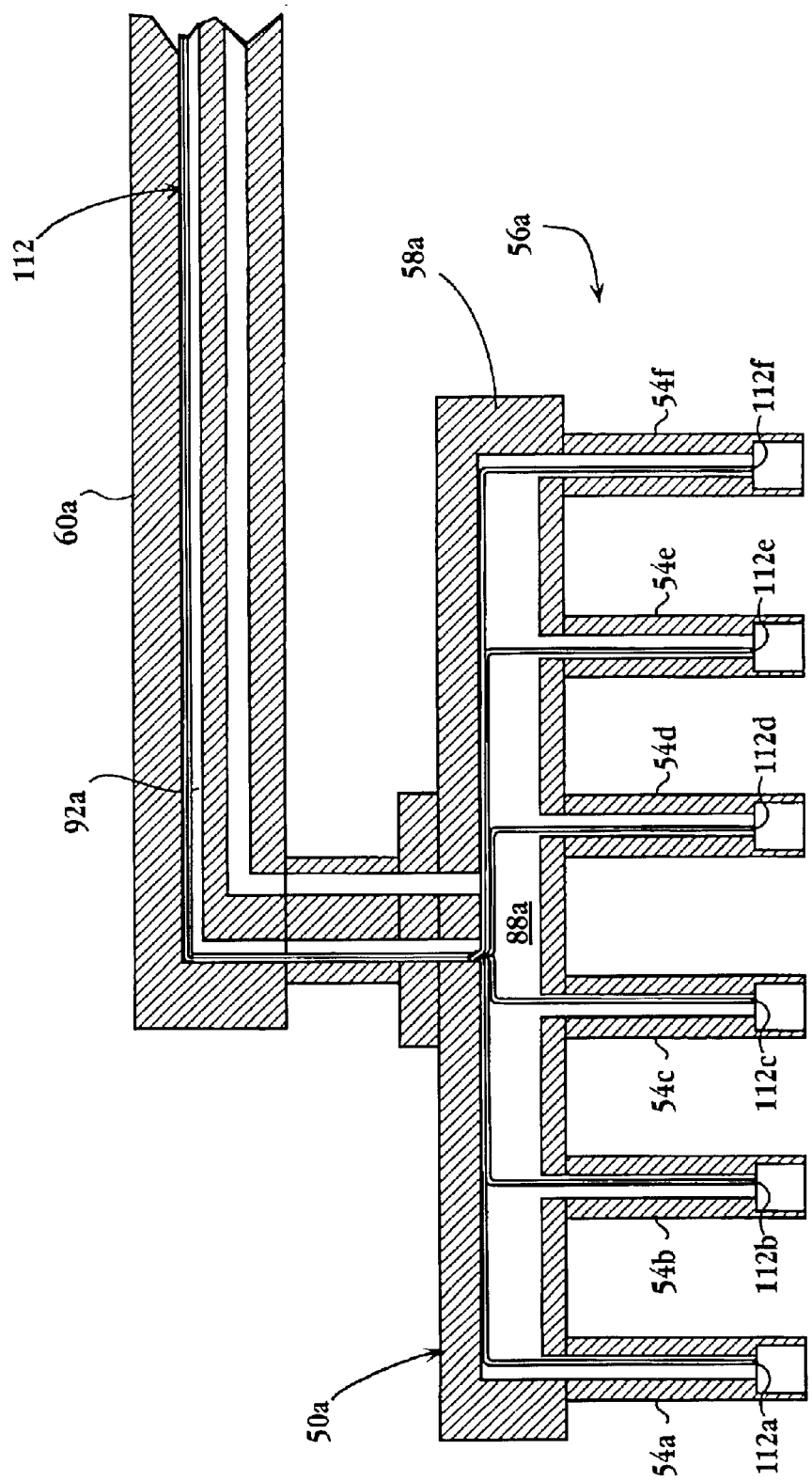

BEAD DISPENSING SYSTEM

This application is a Continuation-in-Part of U.S. application Ser. No. 09/250,697 filed Feb. 16, 1999, now abandoned, which is incorporated herein by reference.

FIELD OF THE INVENTION

The present invention relates to the manipulation of small beads capable of carrying substances such as reagents or samples, and the like. More particularly, the invention provides a method and apparatus for fabricating an array of such beads on a micro-card or plate.

BACKGROUND OF THE INVENTION

Multi-well arrays have long been popular for separately performing numerous chemical and/or biological reactions at substantially the same time. Perhaps the most popular multi-well format in recent years has been the 96-well microplate. Typically, several microliters of reagents are placed in each of the 96 reaction wells, per assay. In an effort to decrease reagent costs, as well as to increase throughput, many laboratory directors are now moving toward the use of even higher-density plates having very small wells, such as 384- and 1536-well formats with wells about 1 millimeter in diameter, or smaller. With the higher density well formats, comes the need for distributing even smaller amounts of substances (e.g. <1 µL) into extremely compact arrays.

Most conventional automated micro-volume deposition systems dispense substances in fluid form, using robotic delivery assemblies. In a typical system, a robot aspirates fluid into one or more ejectors, moves a loaded ejector to a well in a micro-card or plate, and delivers an aliquot of fluid. Commonly used ejectors include "non-contact" devices, such as ink jet nozzles, and "contact" devices, such as a pens or quills. Ink jets, pens, and quills are well-known devices used in a variety of applications. Unfortunately, for the purpose of depositing numerous substances into the wells of a micro-card or plate, each of these devices is associated with certain disadvantages. For example, ink jets generally work fine when the fluid of interest has been carefully optimized for the nozzle. However, when depositing many different fluids through the same nozzle, optimization for each separate fluid is often impractical. As a result, the nozzles can become clogged. With regard to pens and quills, these devices can collide with the well walls, and are generally too slow for cost-effective operations.

The task of delivering micro-volumes of fluidic substances can be especially challenging when the substance deposited at each location is unique to one or only a few positions in the array. Further complications can arise when multiple fluidic substances are serially deposited into each well. For example, liquids can drip and splatter, contaminating reagents in neighboring wells. As another disadvantage, all devices contacting a fluid reagent must be cleaned, or disposed of, before being used with a different fluidic reagent. This is necessary to prevent mixing (i.e., contamination) of one reagent with another. It should be appreciated that multiple rounds of cleaning and aspiration can be time consuming and expensive, as well. This is especially true for applications requiring a large number of different substances. As a further disadvantage, it is often difficult to control the volume of fluid dispensed with a high degree of accuracy. Also, small amounts of dispensed liquid can be difficult to detect with standard imaging systems. Accordingly, dispensing errors can go undetected and, thus, uncorrected.

The need is apparent for an apparatus and process capable of fabricating an array of substances on a micro-card or plate in a relatively fast, efficient and accurate manner.

SUMMARY OF THE INVENTION

One aspect of the present invention provides a system for picking up a plurality of relatively small beads from a supply and transferring them to a desired location.

According to one embodiment, the system includes a plurality of projections, e.g., in the nature of tubes or rods, depending from a support at spaced-apart locations defining an array. Each projection has a lower end region, distal from the support, with a cavity formed therein. Each such cavity is characterized by a lower opening, an upper ceiling region, and a sidewall extending between the lower opening and upper ceiling region. An attraction source, such as a vacuum, electrostatic and/or magnetic force, is operable at each projection end region in a manner effective to draw beads from the supply into the cavities and to releasably retain the beads therein.

In one embodiment, the sidewall about each cavity is formed, at least in part, of a resiliently flexible material, such as tetrafluoroethylene (TFE) tubing, or the like. The resiliently flexible sidewall can have, for example, a generally cylindrical or tubular shape, with both an inner diameter and a longitudinal depth of less than about 1.5 mm. In an exemplary arrangement, intended for use with submillimeter beads, the inner diameter and longitudinal depth are between about 100–1,250 micrometers. In a particularly preferred construction, especially useful in connection with substantially spherical microbeads having a diameter of between about 275–325 micrometers, the inner diameter and longitudinal depth are between about 350–425 micrometers.

In an exemplary arrangement, the sidewall about each cavity has a substantially constant inner diameter along a region extending between its lower opening and its upper ceiling region, such that lines extending longitudinally along confronting inner surfaces of each sidewall are substantially parallel to one another.

According to one embodiment, the lower opening of each cavity has a diameter of between about 100–1,250 micrometers. The longitudinal length of the sidewall, measured from the lower opening to the upper ceiling, is preferably between about 0.50–1.25 times the diameter of the lower opening.

In another embodiment, the lower opening of each cavity has a diameter of between about 250–750 micrometers, and preferably between about 350–425 micrometers. Further in this embodiment, the longitudinal length of the sidewall, measured from the lower opening to the upper ceiling, is between about 0.75–1.10 times the diameter of the lower opening. In one particularly preferred embodiment, the diameter of the lower opening and the longitudinal length of the sidewall are approximately equal.

In one embodiment, the cavity at the lower end region of each projection is configured to receive between about 0.50–1.25 beads, and preferably between about 0.75–1.10 beads. In a particularly preferred embodiment, each cavity can receive one entire bead. The cavities, in this preferred construction, are sized to preclude entry of a substantial portion (e.g., >20%) of a second bead once a first bead has become situated therein.

The system of the present invention can further include a plurality of ampules for containing the bead supply. In a preferred arrangement, a plurality of plastic ampules are disposed in an array alignable with the projection array. Each ampule can be provided with a cover member configured to extend over an upper opening thereof. The covers can be, for example, plastic domes or caps, and/or frangible polymeric membranes (films).

The support from which the projections depend can include, or be attached to, a frame adapted to pivot about a generally vertical axis, rendering the projection array movable along a generally arcuate or circular pathway. The frame can further be adapted for reciprocal linear motion along a generally vertical pathway. By this construction, the projections can be aligned over the ampule array, and each projection can be lowered into a respective one of the ampules.

The ampules can hold any desired reagents. In one embodiment, for example, each ampule holds beads carrying two primers, two probes and buffer for use in real-time PCR. It should be appreciated that the reagents in the various ampules can be the same or different. In one embodiment, one of the ampules holds a plurality of submillimeter beads that carry a first set of analyte-specific reagents, and another of the ampules holds a plurality of submillimeter beads that carry a second set of analyte-specific reagents. The first and second reagent sets can differ from one another, for example, by at least one analyte-specific component.

The cavities at the lower end regions of the projections can be formed, for example, by fitting a resiliently flexible, tubular sleeve, or sheath, over their free ends such that an overhang region is left extending below the terminal end of each projection. In this construction, the overhand region can define the sidewall laterally bounding each cavity and the terminal end of each projection, facing the cavity, can define the upper ceiling region.

According to one embodiment, each of the projections is a capillary tube having an axial lumen extending therethrough. Each lumen, in this embodiment, is provided with a first end that opens into a respective one of the cavities through its ceiling region, and a second end disposed in fluid communication with a pressure-control assembly. The pressure-control assembly can include, for example, a vacuum pump operable to establish a reduced pressure within each of the lumens, and/or a pump operable to establish an increased pressure within each of the lumens. Regarding the latter, such an increased pressure can be utilized to displace (blow out) any beads retained in the cavities.

In one preferred construction, each lumen is formed with an inner diameter at its first end that is smaller than the diameter of a respective cavity into which it opens. For example, each cavity can have an inner diameter, at a location directly adjacent its ceiling region, of greater than 275 micrometers (e.g., between about 300–400 micrometers), and each of the lumens can have an inner diameter at its first end of between about 100–275 micrometers.

A detection system can be used to sense the presence or absence of a bead retained in the various cavities. One embodiment, for example, provides a detection system having a field of view extending along each of the projection end regions. In one particular arrangement, the detection system includes a plurality of elongated light-conductive (optical) fibers. One end of each fiber, in this arrangement, extends along one of the projections and faces a respective cavity. The other end of each fiber can be disposed in communication with a camera device, such as a CCD camera.

The system of the present invention can further include a conduit assembly having a plurality of conduits for separately guiding or funneling a plurality of beads released from the various cavities to desired locations on a substrate (e.g., into wells of a micro-plate or card). In one embodiment, the conduits have (i) large openings at their upper ends disposed in an array having a center-to-center pitch substantially like that of the projection array such that the large openings are generally alignable thereunder, and (ii) small openings at their lower ends.

The small openings can be disposed in an array having a center-to-center pitch substantially like that of the large-opening array, or the two arrays can differ in pitch. In one embodiment, for example, the small openings are disposed in an array having a center-to-center pitch substantially smaller than that of the large-opening array. In one particular arrangement, the center-to-center pitch of the small-opening array is reduced by a factor of at least about 2, and preferably at least about 3, as compared to that of the large-opening array.

In one embodiment, the substrate onto which the beads are deposited is a micro-plate or card having a plurality of wells disposed in an array alignable under the small-opening array of the conduit assembly. For example, the substrate can be a plastic 96-well plate. The plate can be of standard dimensions, or custom dimensions. For example, the plate can have an 8×12 regular rectangular array of wells, with each well having a diameter, at its upper end, of about 1 mm.

The system can further include a detection system operable to sense the presence or absence of a bead in each well of a micro-plate or card. In one embodiment, for example, a detection system is utilized having a field of view extending through each of the conduits and down onto the substrate.

Another aspect of the present invention provides a system for channeling a plurality of beads to desired locations on a substrate, such as a micro-plate or card.

According to one embodiment, the system includes an array of bead supports, such as the previously described projections, with each support being adapted to releasably hold, from above, no more than one bead. A plurality of conduits are disposed under the micro-bead support array. The conduits are provided with (i) large openings at their upper ends disposed in an array having a center-to-center pitch substantially like that of the support array such that the large openings are generally alignable thereunder, and (ii) small openings at their lower ends.

In one embodiment, each of the large openings of the conduit assembly has a diameter of greater than about 1 mm (e.g., between 1–6 mm), and each of the small openings has a diameter of less than about 1 mm (e.g., between 0.15–1 mm).

The small openings can be disposed in an array having a center-to-center pitch substantially like that of the large-opening array, or the two arrays can differ. In one embodiment, the small openings of the conduit assembly are disposed in an array having a center-to-center pitch substantially smaller than that of the large-opening array. In an exemplary arrangement, the center-to-center pitch of the small-opening array is reduced by a factor of at least about 2, and preferably at least about 3, as compared to that of the large-opening array. In another exemplary arrangement, the center-to-center pitch of the large-opening array is greater than about 3 mm (e.g., between about 3–9 mm), and the center-to-center pitch of the small-opening array is less than about 3 mm (e.g., about 1–3 mm).

A parallelogram linkage assembly can be used to support the conduit assembly for reciprocal arcuate movement between a raised position, above and vertically offset from a substrate, and a lowered position, directly over and in close proximity to a substrate. In one such embodiment, a parallelogram linkage assembly is supported on a carousel surface for pivotal movement radially of the carousel's rotational axis. A substrate holding area is also provided on the carousel surface, radially outward of and adjacent to the parallelogram linkage assembly. Further in this embodiment, a stationary rail extends along an inner region of the carousel, having a bearing surface in mechanical communication with the parallelogram linkage arrangement. The construction is arranged to permit the parallelogram linkage assembly to ride along the rail as rotational movement of the carousel advances it. In a preferred arrangement, the bearing surface includes a first arcuate region disposed a first distance from the central axis at a first vertical height, and a second arcuate region disposed a second distance from the central axis at a second vertical height. In this arrangement, the second distance is shorter than the first distance, and the second vertical height is higher than the first vertical height. When the parallelogram linkage arrangement rides along the first arcuate region, the conduit assembly assumes the lowered position over the substrate holding area. When the parallelogram linkage arrangement rides along the second arcuate region, on the other hand, the conduit array assumes the raised position. The bearing surface can also include transition regions bridging the first and second arcuate regions.

According to one embodiment, the substrate is a micro-plate or card having a plurality of wells disposed in an array alignable under the small-opening array of the conduit assembly. For example, the substrate can be a plate having 96 wells, or more. The micro-plate or card can include a pair of spaced-apart indexing bores and/or slots (holes), with each being configured for alignment with a respective indexing pin depending from a lower side of the conduit assembly. Upon inserting the indexing pins into the indexing bores or slots, the conduit assembly's small-opening array becomes substantially aligned with the substrate's array of wells.

In one embodiment, a detection system is provided having a field of view extending into each of the conduits of the conduit assembly. The detection system, in this embodiment, is adapted to sense the presence or absence of a bead on the micro-plate or card under each of the small openings. In an exemplary arrangement, the detection system includes a radiation source, such as a laser, adapted to illuminate the micro-plate or card at locations, e.g., wells, below each of the small openings. The system can further include a plurality of elongated light-conductive (optical) fibers, with each fiber having one end facing, or extending into, a respective one of the large openings to receive light traveling up through a respective conduit and a second end communicating with a camera device, such as a CCD camera.

In another of its aspects, the present invention provides a system for covering an array of wells formed in a micro-plate or card.

According to one embodiment, the system includes a web of an optically clear cover material mounted for movement from a supply reel to a take-up reel. Shearing blades are mounted for reciprocal linear motion along a direction substantially normal to the web for cutting out a portion of the cover material at a region between the supply and take-up reels. A resiliently compliant, generally planar surface is provided between the blades for pressing the web against the upper surface of the micro-card, over the wells.

In one embodiment, a pair of indexing pins extends below the compliant surface. Further in this embodiment, the micro-card is provided with a pair of spaced-apart indexing bores or slots, with each being alignable with one of the indexing pins. Registration of the indexing pins with the bores or slots serves to orient the shearing blade over the micro-card for effecting a cut in the web. In a related embodiment, the shearing blade has a cutting edge defining a quadrilateral, such as a square or rectangle. Upon registering the indexing pins with the indexing bores, a cut can be made in the web having (i) two sides substantially parallel to the side edges of the web and (ii) two sides substantially normal to the side edges of the web. Preferably, the web has a side-to-side width that is longer than the cut along the direction normal to the side edges of the web, so that the web is not severed in two upon making the cut.

A further aspect of the present invention provides an apparatus for delivering a substance (e.g., a liquid solvent or reagent) onto a substrate.

In accordance with one embodiment, the apparatus includes a plurality of elongated conduits disposed in fixed, spaced relation in a common support structure. The support structure can be, for example, a block, tray, plate, frame or the like. In one embodiment, the support structure is made substantially of glass. Each of the conduits is provided with a large opening at one end and a small opening at its other end. Between its two ends, each conduit can have a tapered or funnel-shaped region. The large openings are disposed in an array along one side of the support structure, and the small openings are disposed in an array along an opposite side of the support structure. The large- and small-opening arrays can be arranged with a similar pitch (center-to-center spacing), or they can differ. In one embodiment, the large-opening array is arranged with a center-to-center pitch substantially larger (e.g., greater than about 2:1, and preferably greater than about 3:1) than that of the small-opening array.

In one preferred arrangement, a region of each conduit extending from a respective one of the small openings is of capillary size, such that a liquid placed in contact with the small-opening array can be drawn at least partially into each conduit. For example, the capillary-size region of each conduit can have an inner diameter of less than about 1 mm. In one embodiment, the capillary-size region of each conduit is provided with an inner sidewall that is hydrophilic.

In yet another of its aspects, the present invention provides a method for simultaneously transferring a plurality of beads from one location to another location.

According to one embodiment, the method includes the steps of:

(i) picking up, in a substantially simultaneous fashion, a plurality of beads from a supply and retaining the beads at respective, spaced-apart locations defining an array;

(ii) releasing the beads, in a substantially simultaneous fashion, over a substrate having an array of separate bead-holding regions; and (iii) individually channeling or guiding each of the released beads, in a substantially simultaneous fashion, to a respective one of the bead-holding regions.

The step of picking up beads can be effected, for example, by establishing a reduced pressure (vacuum) at each of the locations, and the step of releasing the beads can be effected by establishing an increased pressure (positive gas flow) at each of the locations.

In one embodiment, the array of bead-holding regions (e.g., wells of a micro-plate or card) has a center-to-center pitch substantially smaller than that of the retained-bead array. In an exemplary arrangement, the center-to-center pitch of the array of bead-holding regions is reduced by a factor of at least about 2, and preferably at least about 3, as compared to that of the retained-bead array.

According to one embodiment the bead supply is provided in an array of plastic capsules or ampules. A cover can be provided over an upper opening of each ampule. The covers can be removed, or punctured, to provide access to the beads. Suitable covers can include, for example, polymeric film-like membranes, or plastic caps/domes.

One embodiment provides, between step (i) and step (ii), a step of inspecting each location of the retained-bead array for the presence of a bead; and picking up and retaining a bead for locations lacking a bead. After step (iii), each of the bead-holding regions can be inspected for beads deposited therein.

In one embodiment, each of the bead-holding regions can be covered with an optically clear film, or the like. The film can be sealed over the bead-holding regions using adhesives and/or heat-sealing techniques.

These and other features and advantages of the present invention will become clear from the following description.

BRIEF DESCRIPTION OF THE DRAWINGS

The structure and manner of operation of the invention, together with the further objects and advantages thereof, may best be understood by reference to the following description taken in conjunction with the accompanying drawings, in which:

FIG. 4(A) is a side elevational view, with a portion broken away and others shown in phantom, of an elongated projection, in the nature of a tube, for use in attracting and retaining reagent-carrying beads, according to an embodiment of the present invention.

FIG. 4(B) is a side elevational view of the projection shown in FIG. 4(A), further illustrating a bead disposed in a cavity at the lower end region of the projection.

FIG. 5 is a side cross-sectional view of one preferred construction for a projection useful in attracting and retaining reagent-carrying beads, as taught by an embodiment of the present invention.

FIG. 8A is a side cross-sectional view of an array of projections, like that of FIG. 1, with each projection having an optical fiber extending therethrough for determining the presence of a bead in a respective cavity at its lower end region, according to an embodiment of the present invention.

DETAILED DESCRIPTION OF THE INVENTION

The following discussion of the preferred embodiments of the present invention is merely exemplary in nature. Accordingly, this discussion is in no way intended to limit the scope of the invention.

One aspect of the present invention provides a system for picking up a plurality of small, reagent-carrying beads from a supply or source area and transferring them onto a substrate, e.g., wells in a micro-card or plate. Generally, the system includes a plurality of projections depending from a movable support structure at fixed, spaced-apart locations. A cavity is provided at a lower end region of each of the projections, defined by a (i) lower opening, (ii) an upper ceiling, and (iii) a sidewall extending between the lower opening and upper ceiling. An attraction source is operable at each of the projection end regions in a manner effective to draw individual beads from the supply into respective cavities and to releasably retain them therein. While retained in the cavities, the beads can be moved from one place to another with movement of the support structure. Once the beads have been positioned at a desired location, they can be released from the cavities. A plurality of conduits can be used to separately guide or channel the beads, once released from the cavities, to desired locations on the substrate.

Figure 1:
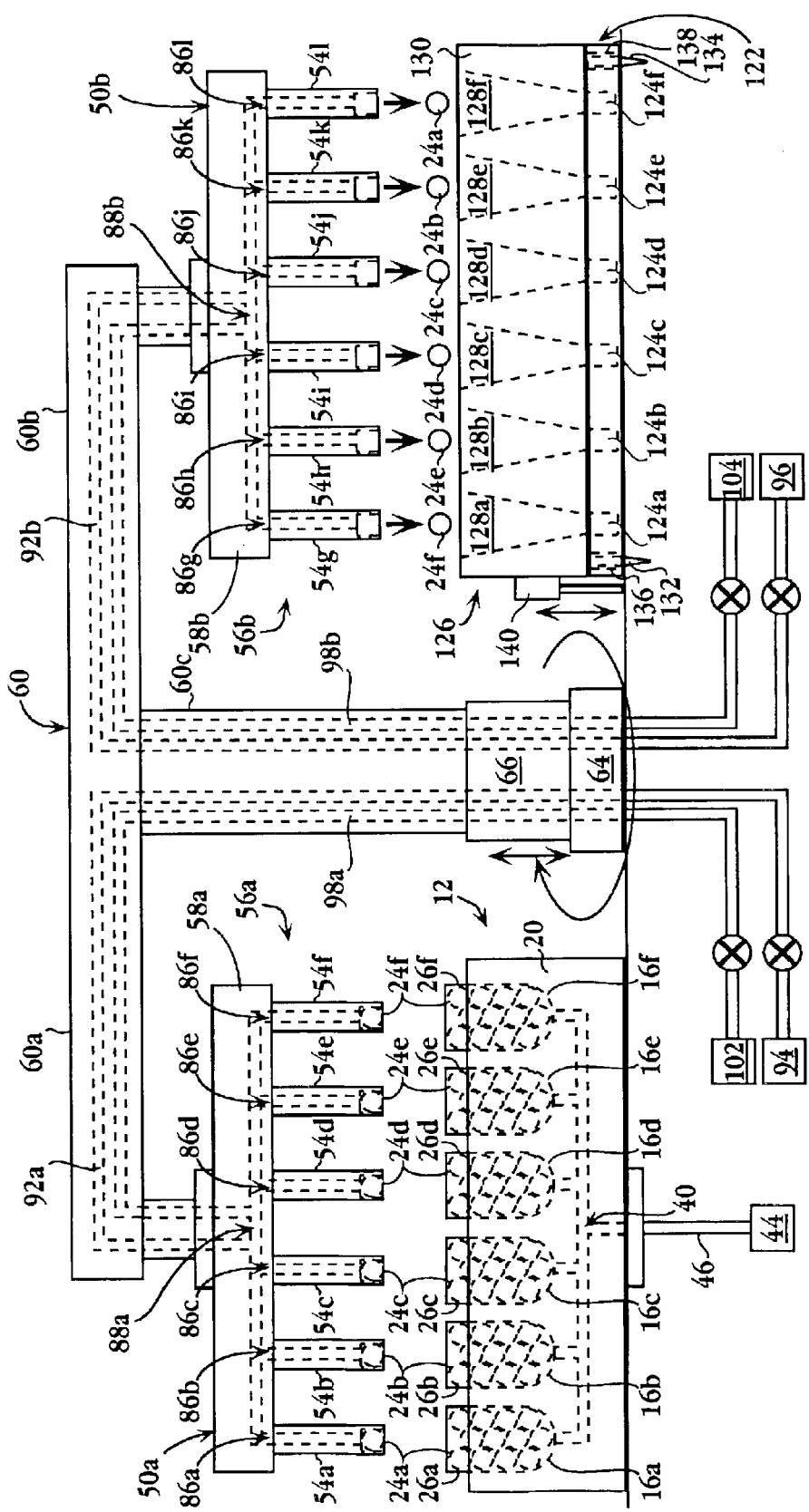
FIG. 1 is a partially schematic side elevational view, with portions shown in phantom, of a system for fabricating an array of reagent-carrying beads on a substrate, constructed in accordance with one embodiment of the present invention.

More particularly, and with initial reference to the exemplary embodiment of FIG. 1, a reagent supply is indicated at 12, having a plurality of spaced-apart reagent-supply locations, arranged in an array. Each reagent-supply location is defined by a well, such as 16a–16f, of a reagent plate 20. While only six such locations, arranged side-by-side in a linear fashion, are visible in the view of FIG. 1, it should be understood that any reasonable number of supply locations can be disposed in any desired spatial configuration. For example, a reagent plate, like plate 20, can include 24, 48, 96, 384, 1024, 1536 wells, or more, with each well being configured to support a plurality of reagent-carrying beads. In such arrangements, the wells will typically be arranged in a regular array, e.g., an 8×12, 16×24, 32×32, or a 32×48 rectangular array, though other layouts are possible. As indicated above, each reagent-supply location 16a–16f can hold a plurality of beads, such as 24a–24f, respectively. Each bead, in turn, can carry a desired reagent.

A wide variety of reagent-carrying beads can be used with the present invention. Generally, the beads should resist substantial physical deformations when exposed for a relatively short time to moderately stressful conditions, e.g., being pulled upon by an attractive force such as a vacuum, or a magnetic or electrostatic field, as discussed more fully below. Certain embodiments, for example, contemplate the use of beads having a substantially rigid outer shell, or a soft gelatinous coating. Several exemplary types of beads are described next.

In one embodiment, the beads are formed by applying a coating material, such as a gelatin, to a reagent core. The coating cures to form a substantially solid shell about the reagent. The coating can be dissolvable or swellable to permit access to the reagent under controllable conditions (e.g., upon exposure to a particular solvent). Guidance for preparing coated beads, or micro-particles, is provided, for example, in: [1] R. Pommersheim, H. Lowe, V. Hessel, W. Ehrfeld (1998), "Immobilation of living cells and enzymes by encapsulation," Institut für Mikrotechnik Mainz GmbH, IBC Global Conferences Limited; [2] F. Lim A. Sun (1980), *Science* 210, 908; [3] R. Pommersheim, J Schrezenmeir, W. Vogt (1994), "Immobilization of enzymes and living cells by multilayer microcapsules" *Macromol Chem. Phys* 195, 1557–1567; and [4] W. Ehrfeld, V. Hessel, H. Lehr, "Microreactors for Chemical Synthesis and Biotechtechnology-Current Developments and Future Applications" in: *Topics in Current Chemistry* 194, A. Manz, H. Becker, Microsystem Technology in Chemistry and Life Science, Springer Verlag, Berlin Heidelberg (1998), 233–252; each expressly incorporated herein by reference.

In another embodiment, a plurality of bead-like particles act as solid supports for the reagents. For example, reagents can be synthesized on the beads, or absorbed thereto. In still a further embodiment, a slurry or dispersion comprised of a reagent and binding material is used to form a plurality of bead-like particles, with each individual bead having a substantially homogenous consistency. Methods for preparing such beads are well known to those skilled in the art.

A plurality of different reagents can be formed into respective collections or groups of reagent beads, referred to herein as "lots." For example, 10,000 different reagents can be formed into 10,000 different bead lots, with each lot comprised of a plurality of substantially like beads carrying a respective reagent. To assist in distinguishing beads from different lots, and to provide a means for quickly determining the type of reagent carried by any one particular bead, beads from each lot can be formed to display a particular, pre-assigned color. For example, yellow beads can carry reagent "A," blue beads can carry reagent "B," and red beads can carry reagent "C." Beads from each lot can be placed at respective reagent-supply locations.

In one embodiment, a plurality of bead lots are formed, wherein each bead includes a reagent core covered with a coating material, such as a gelatin, having well-defined physical and chemical properties. Preferably in this embodiment, all beads in all lots bear substantially the same outer coating (i.e., a "generic" coating), with the coatings for each lot differing only in color, as discussed above. It should be appreciated that this arrangement reduces the risk of equipment contamination due to contact with the reagents themselves. If any residues are left behind as the reagents move through the system, such residues will all be of the same, known coating material. Preferably, the coating material is chosen so that any residues are innocuous to the system. It should further be appreciated that a higher speed for depositing substances can be achieved using such beads, as compared to conventional liquid deposition systems, because the hardware delivering the beads will not require frequent cleaning, nor is time spent aspirating fluids.

While beads of substantially any shape can be used with the present invention, beads having a generally spherical geometry are particularly well suited for use herein. Also, the system of the invention can be used with beads of various sizes. For example, one embodiment contemplates the use of spherical beads having a diameter of less than about 1 mm. In one such arrangement, each bead is formed with a diameter of between about 275–325 micrometers, and most preferably about 300 micrometers. In another embodiment, the beads are larger, such that each bead substantially fills one well of the reagent plate. For example, each bead can have a diameter of between about 1.0–4.0 mm, and preferably about 3.7 mm. Each well of the reagent plate, in turn, can be configured with an inner diameter slightly larger than the diameter of a bead. The lower end of each well, in this embodiment, can be shaped to complement the contour of the bead's outer surface.

The beads can carry any desired reagent. As used herein, the term "reagent" can refer to a single substance, or a grouping of substances. According to one preferred embodiment, the reagent carried by each bead includes components useful for real time fluorescence-based measurements of nucleic acid amplification products (such as PCR) as described, for example, in PCT Publication WO 95/30139 and U.S. patent application Ser. No. 08/235,411, each of which is expressly incorporated herein by reference.

In an exemplary arrangement, each bead carries an analyte-specific reagent effective to react with a selected analyte that may be present in a sample. For example, for polynucleotide analytes, the analyte-specific reagent can include first and second oligonucleotide primers having sequences effective to hybridize to opposite end regions of complementary strands of a selected polynucleotide analyte segment, for amplifying the segment by primer-initiated polymerase chain reaction. The analyte-specific detection reagent can further include a fluorescer-quencher oligonucleotide capable of hybridizing to the analyte segment in a region downstream of one of the primers, for producing a detectable fluorescent signal when the analyte is present in the sample.

A plurality of beads from the same or substantially identical lots can be packed into an ampule or capsule. A plurality of such ampules (e.g., tens, hundreds, thousands, or more) can be dispensed into respective, designated wells of a multi-well plate, with the various ampules containing the same or different reagents, as desired. As depicted in FIG. 1, for example, a plurality of plastic ampules 26a–26f, each holding beads carrying a different reagent, are removably seated in respective wells, 16a–f, of reagent plate 20. Ampules of any desired size and shape can be used. One arrangement, for example, contemplates the use of generally bullet-shaped ampules having an open top and a rounded, closed bottom. Exemplary dimensions for each ampule are as follows: (i) about 10 mm in height, (ii) an outer diameter of about 3.7 mm, and (iii) an inner diameter of about 3.0 mm. About 1,000 substantially spherical reagent beads, each having a diameter of about 300 micrometers, can be loaded into each such ampule. An exemplary reagent plate, useful for holding the just-described ampules, is configured with an array of wells (e.g., an 8×12, 16×24, or 32×32 array), with each well having an inner diameter of about 4.0 mm and a depth of between about 6–9 mm.

The ampules can be placed in the wells of the reagent plate in any suitable manner. In one embodiment, an operator manually places the ampules in the wells. In another embodiment, the ampules are serially dispensed from respective containers supported in an array of holding cells disposed above the reagent plate, as taught in U.S. application Ser. No. 09/251,232 filed Feb. 16, 1999 and expressly incorporated herein by reference.

Figure 2:
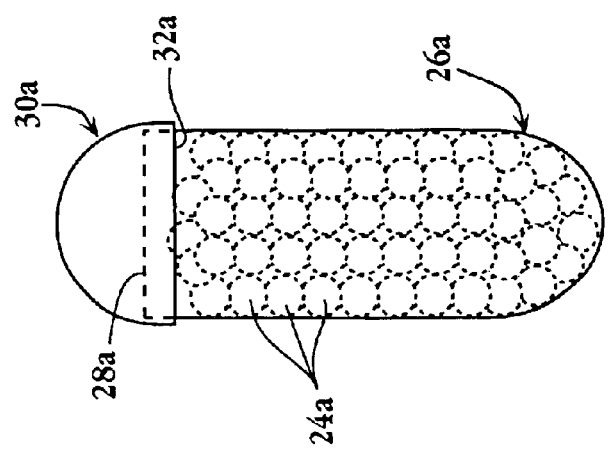
FIG. 2 is a side elevational view, with portions shown in phantom, of an ampule containing a plurality of reagent-carrying beads, and having a dome-like cover member over an upper opening, according to an embodiment of the present invention.

Each ampule can be provided with a cover member over an upper opening thereof. The cover member can be, for example, a removable cap or dome, such as 30a of FIG. 2, having an open end 32a configured to fit snugly about an opening defined by an upper rim, or lip, 28a of an ampule 26a. Or, a sheet-like film or membrane, such as 34a of FIG. 3(A), can be applied to an upper rim 28a about the opening of an ampule 26a. For example, a polymeric film, such as a polystyrene, polyester, polypropylene or polyethylene film, between about 0.05–0.40 millimeters thick, can cover the upper opening of each ampule. In one embodiment, the cover is a thin polyvinylidene chloride (PVDC) film, such as that sold under the trade name SARAN WRAP by Dow Chemical Co., (Midland, Mich.).

As described more fully below, access to the beads can be gained, for example, by displacing the covers using the projection array.

In one embodiment, the cover member over each ampule forms a substantially airtight seal, sequestering the contents of the ampule from the external atmosphere. The seal can be effected or enhanced, for example, using conventional adhesives, elastomers and/or by heating-sealing techniques. In an exemplary arrangement, frictional engagement between a plastic dome-shaped cap and the upper region of a plastic ampule is sufficient to provide an airtight seal. The sealed ampules can further contain an inert gas, such as nitrogen or the like, surrounding the beads.

In another embodiment, each cover member is primarily designed to prevent against spillage, or other loss, of a respective ampule's contents. In this embodiment, the interface between each cover member and its respective ampule is not necessarily airtight.

To prevent against inadvertent dislodgment of the seated ampules, means can be provided for holding the ampules in place at each reagent-supply location. For example, FIG. 1 shows a vacuum manifold, indicated generally at 40, formed in plate 20 under wells 16a–16f. Manifold 40 includes a plurality of generally vertical passageways that communicate a central chamber of the manifold with the bottom regions of respective wells 16a–16f. It should be noted that the uppermost end of each vertical passageway, which opens into a respective well, has a smaller diameter than the outer diameter of a seated ampule. A pressure-control source, such as vacuum pump 44, is disposed in fluid communication with a lower region of manifold 40 by way of a connector line, denoted as 46. Upon activating pressure-control source 44, a reduced pressure can be established at the bottom region of each well 16a–16f. The reduced pressure is effective to draw upon the bottom of each seated ampule 26a–26f, thereby preventing dislodgment from the wells. Upon deactivating pressure-control source 44, the ampules can be readily removed from the wells, if desired.

Instead of loading the beads into an ampule or capsule, which is then placed at a reagent-supply location, one embodiment contemplates placement of the beads directly into the wells, or other holding areas, of a reagent plate or the like. The wells of the reagent plate, in this embodiment, can be formed with fully closed bottoms.

With continuing reference to the embodiment of FIG. 1, a pair of bead extractors, denoted generally by the reference numerals 50a and 50b, are adapted for positioning at respective locations that are elevated with respect to reagent plate 20. Each extractor 50a, 50b includes a plurality of projections, such as 54a–54f and 54g–54l, depending from a respective support structure, 58a and 58b, at fixed, spaced-apart locations. Each projection can be shaped, for example, as an elongated nub, tube, rod, or the like, extending from the support. Preferably, the longitudinal axes of projections 54a–54f, 54g–54l are disposed such that they are generally parallel to one another.

Projections 54a–54f, 54g–54l can be formed integrally with their respective support structures 58a, 58b, or they can be formed separately and attached by any suitable means. According to one embodiment, for example, a plurality of separately-formed projections bear threads at one end for mating engagement with respective threaded bores extending into the lower side of a respective support.

Together, each group of projections 54a–54f, 54g–54l defines a respective projection array, denoted as 56a and 56b. Each projection array 56a, 56b is configured with substantially the same center-to-center spacing as the array of reagent-supply locations (wells) 16a–16f in reagent plate 20. Preferably, each projection array 56a, 56b includes as many projections as the reagent plate has reagent-supply locations, or a substantial fraction thereof. By this construction, each projection array 56a, 56b is alignable with locations of the supply.

A substantially T-shaped frame, denoted generally as 60, supports both extractors 50a, 50b. More particularly, frame 60 includes an upper, horizontal crossbar, having co-linear arm portions 60a, 60b. The upper side of each support structure 58a, 58b is rigidly attached to an outer end region of a respective arm 60a, 60b. A rotation motor, depicted schematically at 64, under the direction of a control computer (not shown), is adapted to rotate a central vertical shaft 60c of frame 60 about its longitudinal axis, thereby rendering movable the projection arrays 56a, 56b along arcuate or circular pathways. In addition, extractors 50a, 50b are adapted for reciprocal linear motion along respective vertical pathways. Such movement can be effected, for example, by way of a linear motor, as at 66, operatively arranged to move shaft 60c up and down along its longitudinal axis. As with rotation motor 64, linear motor 66 is preferably adapted for operation under the direction of a control computer.

The range of motion, just described, permits a number of operations, such as (i) aligning a projection array with the ampule array, (ii) lowering the projections into respective ampules to attract and retain reagent beads, (iii) lifting retained beads above the ampule array, and (iv) transferring the retained beads to a desired location. Such operations are set out in greater detail below.

It should be appreciated that any reasonable number of extractors can be employed. For example, instead of using two extractors, as described above, one embodiment of the invention includes only a single extractor. Further embodiments, on the other hand, contemplate the use of several (e.g., 3, 4, 5, 6, or more) extractors. The number of crossbar or arm assemblies for the supportive frame, in these embodiments, will be determined by the number of extractors included in the system.

With reference to the enlarged view of projection 54a shown in FIG. 4(A), a cavity, denoted as 70, is provided at the projection's lower end region. In this embodiment, cavity 70 is defined by (i) a lower opening formed by a terminal rim or lip 72, (ii) an upper ceiling region 74, and (iii) a sidewall 76 extending between the lower opening and upper ceiling. The composite of these elements is generally that of an inverted cup-like structure.

Cavity 70 can be constructed, for example, by forming an axial bore into one end of an elongated rod or tube. The rod or tube can be of any suitable material, such as plastic, glass, aluminum, and the like. In one embodiment, a bore is formed in a polyurethane tube. The bore can be formed in any manner, e.g., drilling with a bit having a diameter sufficiently smaller than the outer diameter of the tube or rod. Where a tube already having a longitudinally extending bore or lumen, such as at 86a in FIG. 4(A), is used, cavity 70 can be formed by drilling a counterbore into an end of the tube, with the counterbore having a diameter greater than the inner diameter of the lumen 86a, yet smaller than the outer diameter of the tube.

The cavity at the end region of each projection is preferably configured to receive no more than about one entire bead. FIG. 4(B), for example, shows a single bead 24a contained within cavity 70. Notably, in this embodiment, cavity 70 is substantially filled by bead 24a, leaving insufficient room to accommodate a second entire bead, or even a substantial portion of a second bead. It should be appreciated that the particular size of the cavity will generally be determined by the size of the beads used with the system. Thus, for substantially spherical beads a little less than 1 mm in diameter (e.g., 0.75–0.95 mm), a suitably sized cavity can have an inner diameter, from one sidewall region to a directly opposing sidewall region, of about 1 mm. The longitudinal depth, from the ceiling region to the lowermost opening, will generally be from between about 50%–125% of the size of the inner diameter of the cavity. Accordingly, in this example, the longitudinal depth is between about 0.50–1.25 mm. Preferably, the longitudinal depth is between about 75%–100% of the cavity's inner diameter; and most preferably the longitudinal depth and inner diameter are approximately equal. In a particularly preferred embodiment, wherein substantially spherical beads having a diameter of between about 275–325 micrometers are utilized, each cavity is configured with both an inner diameter and longitudinal depth of between about 330–500 micrometers, and most preferably about 375 micrometers. The cavity, in this embodiment, is formed at the end of a polyurethane rod or tube having an outer diameter of about 0.5 mm.

FIG. 5 shows one preferred construction for a projection, denoted generally as 54a', for use in a projection array, such as 56a and 56b of FIG. 1. In this embodiment, each cavity 70' is formed, for example, by fitting a hollow sheath, or sleeve, 80 over the end of an elongated tube or rod 82, and leaving an overhang region of the sheath, as at 80a, extending below a terminal end 82a of the tube. In this arrangement, the overhang region 80a of sheath 80 defines sidewalls 76', and the terminal end 82a of the tube 82, facing cavity 70', defines a ceiling region 74'. Frictional engagement of sheath 80 about the end of tube 82 can maintain the relative positioning of these elements. Optionally, conventional adhesives, abrasives, and/or shrink-fitting techniques can be used to hold sheath 80 in place on tube 82. Tube 82 can be constructed, for example, of a substantially rigid material, such as glass, plastic, metal, and the like. Sheath 80 can be formed, for example, from a material that is resiliently expandable and flexible, such as tetrafluoroethylene (TFE), or the like. Suitable tubing, for use in constructing sheath 80, is available commercially, for example, from McMaster-Carr Supply Co. (Chicago, Ill.) under the product name "Thinwall Teflon TFE Spaghetti Tubing."

The ceiling region 74 can have any suitable shape or contour. In the exemplary arrangement of FIG. 4(A), ceiling region 74 is generally conical or funnel-shaped, with an inwardly and upwardly sloped surface (along the direction away from the lower end of the tube). In a similar arrangement (not shown), the ceiling region is generally horn-shaped. In still a further embodiment, the surface of the ceiling region is substantially planar, as shown, for example, at 74' in FIG. 5.

As previously indicated, an attraction source is operable at each of the projection end regions in a manner effective to draw individual beads from the supply into respective cavities and to releasably retain them therein. In a typical operation, the attraction source will be engaged after an array of projections, such as 56a or 56b (FIG. 1), has been aligned with a corresponding array of reagent-supply locations, such as wells 16a–16f, and the projections have been lowered to respective positions proximate a plurality of reagent beads, such as 24a–24f, held therein. The attraction source can be, for example, a reduced pressure (vacuum), an electrostatic force, and/or a magnegtic force. In one preferred embodiment, the attraction source is a vacuum. In the embodiment of FIG. 1, for example, each of the projections, 54a–54f and 54g–54l, is a capillary tube having an axial lumen, respectively denoted as 86a–86f and 86g–86l, extending therethrough. As best seen in the detailed view of FIGS. 4(A)–4(B), lumen 86a provides a passageway for a vacuum to extend longitudinally through the projection 54a. Lumen 86a has a lower end that opens into a respective cavity 70 through a central area of ceiling 74. At its lower end, the inner diameter of lumen 86a is smaller than the diameter of cavity 70, at a location adjacent the ceiling region 74. In an exemplary arrangement, each of the cavities has a diameter of at least 275 micrometers (e.g., between about 300–350 micrometers, and preferably about 325 micrometers), and each of the lumens has an inner diameter at its lower end of less than 275 micrometers (e.g., between about 230–270 micrometers, and preferably about 250 micrometers).

In an alternative embodiment, a plurality of beads are attracted to, and retained at, respective projection end regions using electrostatic means. Techniques for attracting and retaining micro-beads using an electrostatic force are disclosed, for example, in U.S. Pat. Nos. 5,788,814 and 5,846,595; each of which is expressly incorporated herein by reference.

Referring again to FIG. 1, the upper end of each lumen 86a–86f, 86g–86l leads to a respective manifold, such as 88a and 88b, formed in support structures 58a, 58b. Each manifold 88a, 88b, in turn, is disposed in fluid communication with a respective pressure-control source. For example, manifold 88a can communicate with vacuum pump 94 via flow line 92a, and manifold 88b can communicate with vacuum pump 96 via flow line 92b. Each vacuum pump 94, 96 is operable, e.g., under the direction of a control computer (not shown), to establish a reduced pressure in a respective line 92a, 92b and, consequently, within a respective array of lumens 86a–86f, 86g–86l.

The manifolds can be of a generally monolithic construction, e.g., molded of plastic or metal; or they can be assembled from sub-component parts. Regarding the latter, one embodiment (not shown) contemplates a manifold comprised of several sub-component layers, stacked one on top of the other. One such muti-layered arrangement includes a rectangular frame member, having a central opening, sandwiched between upper and lower rectangular plate members. Together, the layers form a box-like structure having a central open region, or chamber. Particularly, the upper surface of the lower plate member defines a floor region; the inner edge of the rectangular frame member provides lateral sidewalls; and the lower surface of the upper plate member defines a ceiling region. A rectangular gasket can be interposed between confronting regions of the frame member and each plate member to promote airtight interfaces. The lower plate can be formed with an array of bores extending fully between its two broad surfaces. Each bore can be suitably threaded to receive, from below, a threaded end of a respective tubular projection, and to communicate a lumen extending longitudinally through such projection with the region (chamber) above the plate. Conventional washers and/or gaskets can be used to promote an airtight interface between each projection and the lower plate. The upper plate, which can be attached to a rotatable frame, such as 60, can have one or more conduits formed therethrough for communicating the main chamber with a like number of remotely positioned pressure-control sources.

In an exemplary operation, wells 16a–16f of reagent plate 20 are loaded with respective ampules 26a–26f, each of which contains a plurality of beads 24a–24f carrying a particular reagent. A projection array, such as 56a, is then aligned with the array of wells 16a–16f in plate 20. This can be accomplished, for example, by placing reagent plate 20 at a location underlying the arcuate or circular pathway along which the array 56a moves when the central vertical shaft 60c of frame 60 is rotated about its longitudinal axis. Rotational motor 64 can then rotate frame 60 until array 56a assumes a position directly over, and in alignment with, the ampules 26a–26f of plate 20. Next, linear motor 66 can lower the projections 54a–54f toward respective ampules 26a–26f.

Figure 3B:
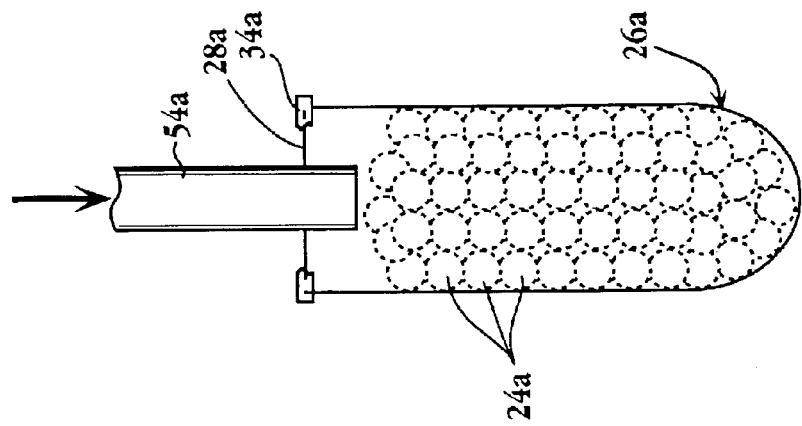
FIG. 3(B) is a side elevational view of the ampule of FIG. 3(A), further showing an elongated projection, in the nature of a tube, that has punctured the cover member to gain access to the beads contained therein, as taught by an embodiment of the present invention.
Figure 3A:
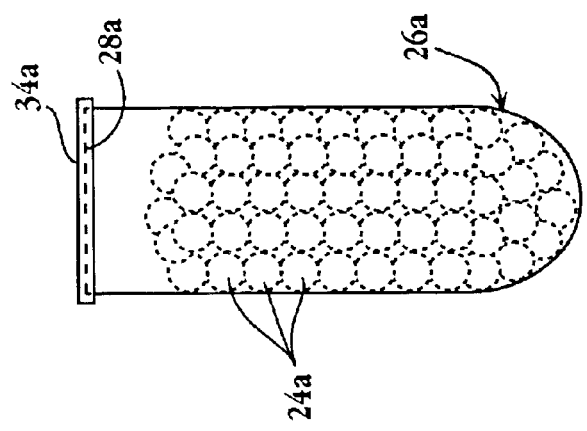
FIG. 3(A) is a side elevational view, with portions shown in phantom, of an ampule containing a plurality of reagent-carrying beads, and having a film-like cover member over an upper opening, according to a further embodiment of the present invention.

If the ampules are provided with cover members, such as dome 30a (FIG. 2) or film 34a (FIG. 3(A)), then the cover members must be displaced from the opening region of each ampule, at least partially, in order to access the beads therein. With regard to film-type covers, e.g., a thin polymeric membrane, as the projections 54a–54f are lowered, each can engage and rupture the cover, as exemplified in FIG. 3(B). In this way, all of the covers in the array can be displaced at substantially the same time.

Figure 6:
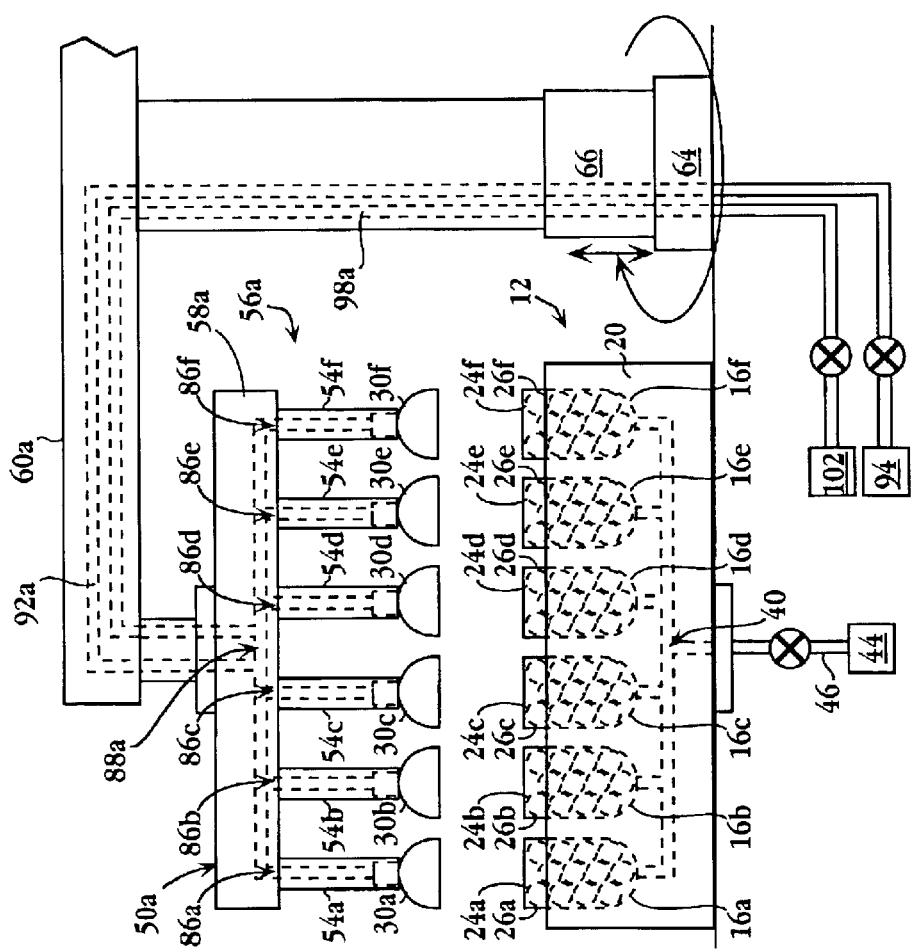
FIG. 6 is a partial view of the system depicted in FIG. 1, illustrating the simultaneous removal of a plurality of dome-like cover members from a like number of ampules containing a bead supply, according to an embodiment of the present invention.

An exemplary process for removing cap or dome-type covers is depicted in FIG. 6. This process is particularly useful for simultaneously removing a plurality of covers that are frictionally fitted about the upper rim or lip region of respective ampules; the frictional engagement being such that each cover and ampule can be pulled apart using only a moderate amount of force. Projections 54a–54f are lowered until each engages the top of a respective dome-type cover 30a–30f. Pressure-control source 44 is actuated to generate a reduced pressure in flow line 46 and, thus, in manifold 40 and at the lower regions of wells 16a–16f. Pressure-control source 94 is actuated to generate a reduced pressure in flow line 92a and, thus, in manifold 88a and at the lower regions of projections 54a–54f. Responsive to the vacuum forces, the bottom of each ampule is drawn downward against the lower region of its respective well, and the top of each cover member is drawn up against a lower rim or lip of a respective projection.

Maintaining a vacuum hold on the domes, projections 54a–54f can be lifted, as exemplified in FIG. 6, thereby pulling domes 30a–30f off of, and away from, ampules 26a–26f and exposing beads 24a–24f. Once the domes have vertically cleared the ampules, rotational motor 64 can rotate frame 60 until the domes are positioned over a depository area (not shown). At this point, the vacuum can be discontinued, permitting the covers to fall, for example, into a collection container (not shown). Rotational motor 64 can then rotate the projection array back into alignment with the ampule array.

Referring again to FIG. 1, once the covers have been removed, or in the event that no covers are utilized, the projections 54a–54f can be lowered to respective positions proximate the beads 24a–24f in the various ampules 26a–26f. Pressure-control source 94 can be actuated to generate a vacuum reaching through each of lumens 86a–86f to a respective cavity, such as cavity 70 of FIGS. 4(A)–4(B), at the lower end region of each projection. The vacuum force that is established at the lower end region of each projection is sufficiently strong to attract a reagent bead from a respective ampule 26a–26f, and to retain the bead in a cavity of the projection. In one embodiment, for example, a pressure of about 15 psi is established at each projection end region to attract and retain spherical beads, each about 300 micrometers in diameter, in a cavity measuring about 325 micrometers in diameter and longitudinal depth.

FIG. 4(B), for example, shows a spherical bead 24a that has been drawn into cavity 70 by a vacuum force pulling in a direction extending up through lumen 86a. The relatively large diameter of bead 24a, compared to the diameter of lumen 86a, as well as the bead's resistance to significant physical deformation, prevents the bead from being sucked up into lumen 86a. As also exemplified in FIG. 4(B), owing to the conical or funnel shape of ceiling region 74, bead 24a becomes situated at an upper, central area of cavity 70.

In one embodiment (not shown), as the projections are being lowered into the ampules, with a reduced pressure established at each projection end region, a stream of gas is directed upwardly from a bottom region of each ampule in a fashion effective to blow beads up towards the projections. For example, a small hole can be formed through the bottom of each ampule. A gas-permeable membrane can cover each hole. Although permeable to gases (e.g., air), the membrane is configured to prevent beads from falling out through the holes. Flow lines can communicate a positive-pressure pump with the various holes. A partial cover can extend over an upper region of each ampule that permits passage of a projection, but prevents beads from being blown past the projections and out through the top of the ampules.

Figure 7:
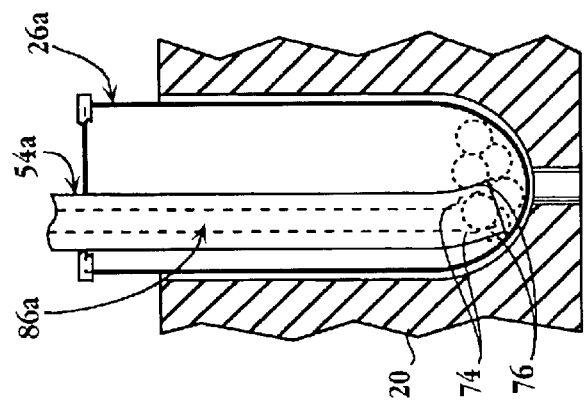
FIG. 7 is a side elevational view, with portions shown in phantom, of a projection, in the nature of an elongated tube, having a resiliently flexible lower end region that can bend when pressed against the bottom region of an ampule, in accordance with an embodiment of the present invention.

As previously noted, one embodiment of the invention contemplates a resiliently flexible lower portion for each projection of the projection array. With reference to projection 54a of FIG. 7, for example, sidewall 76 is formed of a resiliently flexible material, while the rest of the projection, above sidewall 76, is made of a substantially rigid material, such as glass, plastic or metal. This construction permits the lower end region of the projection to bend as it encounters the interior contours of an ampule, such as the curved or rounded bottom region of ampule 26a. This feature is especially useful when only one or a few beads remain in an ampule, since the opening at the projection's end region can bend to face beads gathered in a lower central region of the ampule.

Referring again to FIG. 1, once projections 54a–54f have attracted and retained respective beads 24a–24f from supply 12, linear motor 66 can vertically raise the projections, along with the retained beads, clear of plate 20. Rotational motor 64 can then rotate vertical shaft 60c of frame 60 about its central axis so that the beads, retained on the projection array, are moved to a deposit location. At this point, the vacuum retaining force can be discontinued. For some applications, the force of gravity, alone, will be sufficient to cause each bead to fall from a respective cavity down to a substrate at the deposit location. In other applications, it may be desirable to further urge the beads out of the cavities. In this regard, one embodiment contemplates the establishment of an increased pressure in the manifold above each projection array. The pressure increase is sufficient to cause gas to flow down through the lumen of each projection, thereby "blowing" the beads out of the cavities. A pressure-control source in communication with the manifold above each projection array can effect the pressure increase. As shown in FIG. 1, for example, pump 102 can communicate with manifold 88a via flow line 98a; and pump 104 can communicate with manifold 88b via flow line 98b. Upon activating one of the pumps and generating an increased pressure in a respective manifold, gas will flow downward through the lumens of a respective projection array in a manner tending to blow any retained objects away from the projection end regions.

Detection instrumentation can be included in the system of the invention for monitoring the various operations. In one embodiment, for example, means are provided for determining whether or not a target object, such as a cover member or bead, is present at the lower end region of each projection. In an exemplary arrangement, cessation of gas flow and/or attainment of an expected (predetermined) low-pressure value in the vacuum flow lines can be used as an indicator that each projection has properly engaged and attracted a target object, such that a substantially airtight seal is formed across the lower opening of each projection. If gas continues to flow through a vacuum line, and/or a higher than expected pressure is measured in a vacuum line, then it is possible that at least one of the projections failed to attract and retain a target object. A conventional gas-flow and/or pressure sensor (not shown) can be located along the flow lines for this purpose. The sensor(s) can be read by an operator, and/or communicate with a control computer. In the latter case, the computer can alert an operator to a potential error, and/or automatically initiate corrective actions.

In another exemplary arrangement, the means for determining the presence of a target object at the lower end region of each projection includes a visual detection assembly. As will become apparent, this arrangement is particularly useful in connection with target objects that are substantially opaque or just slightly translucent. Referring now to FIG. 8A, for example, a bundle of light-conductive fibers, denoted generally as 112, can extend through a flow line 92a leading to a projection array 56a. In manifold 88a, above the projection array, the individual fibers 112a–112f of bundle 112 diverge and extend towards respective projections 54a–5f. Each individual fiber is arranged with a first, or "receiving," end extending at least partially into the lumen of a respective projection, and with its terminal face at this end generally directed toward a respective cavity at a lower end region thereof. A radiation source (not shown) can provide light, direct or reflected, that can pass up into each projection, toward such receiving ends, when the projection end region is empty and clear. In one preferred embodiment, a diffuse light source, e.g., a fiber-optic bundle, illuminates substantially the entire upper surface of the reagent plate. Diffusely reflected light, in turn, irradiates each projection end region, from below. The second, or "transmitting," end of each fiber is disposed in communication with a camera device (not shown). In this regard, the fibers can be bundled and supported at their second end such that their terminal faces generally define a plane that is proximate to, and generally parallel with, a planar array of photo-detectors of the camera device. One or a few of the photo-detectors can be assigned to each fiber in the transmitting-end bundle. In an exemplary arrangement, the detector array is part of a CCD having a range of view that is generally confined to a respective grouping of fiber terminal-end faces.

A properly attracted and retained object will extend across a section of the projection's lower end region, thereby blocking light from reaching the receiving end of a respective fiber. Consequently, the photo-detector(s) assigned to such fiber will not receive light (above background). In the absence of an object blocking a section along the projection's terminal end region, on the other hand, light will reach a respective fiber's receiving end and will travel to its transmitting end. From the transmitting end, the light will impinge upon one or more assigned photo-detectors. The photo-detector(s) can then produce an output signal that can be visualized on a CRT screen, or the like, for inspection by an operator.

The output signals can produce bright spots at pre-assigned locations of an otherwise dark CRT screen. Thus, a bright spot on the screen can be used to alert an operator to the absence of a target object at the end region of a particular projection. Alternatively, or in addition, the output signals can be transmitted through an appropriate interface to a control computer. The computer, then, can alert an operator to any projections that have apparently failed to pick up a target object, and/or automatically initiate corrective actions.

In one embodiment, a standard optical fiber having a diameter of between about 30–70 micrometers, and preferably about 50 micrometers, extends into the longitudinal lumen of each projection. Suitable optical fibers are commercially available, for example, from Edmund Scientific Co., (Barrington, N.J.). Each lumen, in this embodiment, can have a diameter of between about 230–270 micrometers, and preferably about 250 micrometers. The transmitting end of each fiber, in turn, can be disposed for communication with one or several photo-detectors of a CCD camera. Any of numerous commercially available CCD cameras can be used in the present invention, and suitable cameras can readily be chosen by those skilled in the art. One particular CCD camera, contemplated for use herein, is available commercially under the trade name PANASONIC GP-KR222.

Rather than running only a single fiber into the lumen of each projection, as shown in FIG. 8A, it should be appreciated that any reasonable number (e.g., 2, 3, 4, 5, or more) of fibers can be employed. Various factors that can be considered in determining an appropriate number of fibers to use include (i) the outer diameter of each fiber, (ii) the inner diameter of the respective lumens, (iii) the inner diameter of the flow lines passing through the supportive frame, and (iv) the number, size and spatial configuration of the photo-detectors in the camera device. Importantly, for those embodiments relying upon a vacuum extending through each projection to attract and retain the beads, the fibers should not substantially hinder gas flow through the various flow lines, manifolds and projection lumens. Preferably, any reduction in flow rate due to the presence of the fibers is less than about 50%.

With further regard to the optical fibers, instead of running each fiber through a flow line passing through the frame structure and into the lumens of the various projections, as illustrated in FIG. 8A, one embodiment (not shown) provides a small bore formed through an upper region of each projection through which an end region of a fiber can be passed. In an exemplary construction, each projection includes a plastic top portion with a metal tube extending therefrom. A small bore is drilled through the metal part of each projection, dimensioned to receive one end of an optical fiber. In this embodiment, each fiber forms a substantially airtight seal with its respective bore so as not to interfere with the establishment of a desired pressure (e.g., a vacuum) in the system.

Rather than directing light up through each projection, the detection system can be arranged to operate in a "reverse" manner from that described above. That is, the fiber ends distal from the projections can act as "receiving" ends communicating with a light source. The fiber ends in the projections, on the other hand, can act as "transmitting" ends adapted to direct light down and out of each projection end region. In operation, prior to picking up objects with the projections, a camera can image the projection end regions, from below. For example, the central frame can be rotated about an angle sufficient to pass each projection over a linear photo-detector array. Those projections that have light passing out of their lower end regions are determined to be empty and clear—i.e., available for picking up an object. After a pick-up operation, the camera can again image the projection end regions. A properly picked up and retained object will block light from reaching the camera's photo-detector array. A pick-up failure is indicated for any projections that have light passing out of their lower end regions. Corrective actions can be taken, e.g., a reload attempt, in the case of a pick-up failure.

Figure 8B:
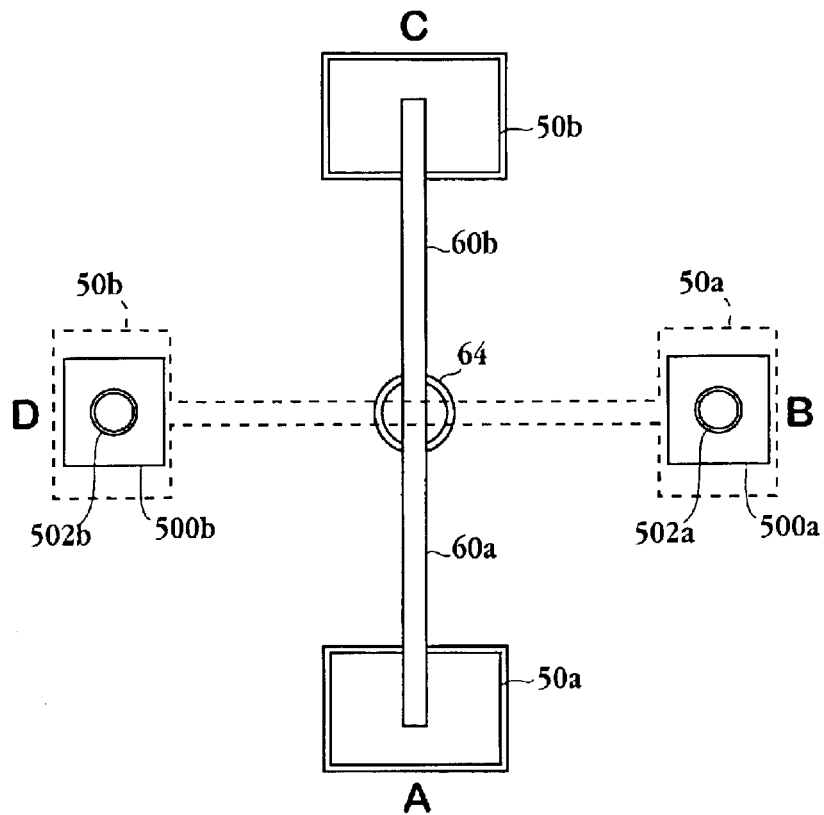
FIG. 8B a top view of a horizontal crossbar and bead extractors of the system shown in FIG. 1, with portions of the bead extractors broken away in the phantom-depicted positions to illustrate cameras employed to capture an image of the lower end of a projection array for determining the presence or absence of a target object, according to an embodiment of the invention.
Figure 8C:
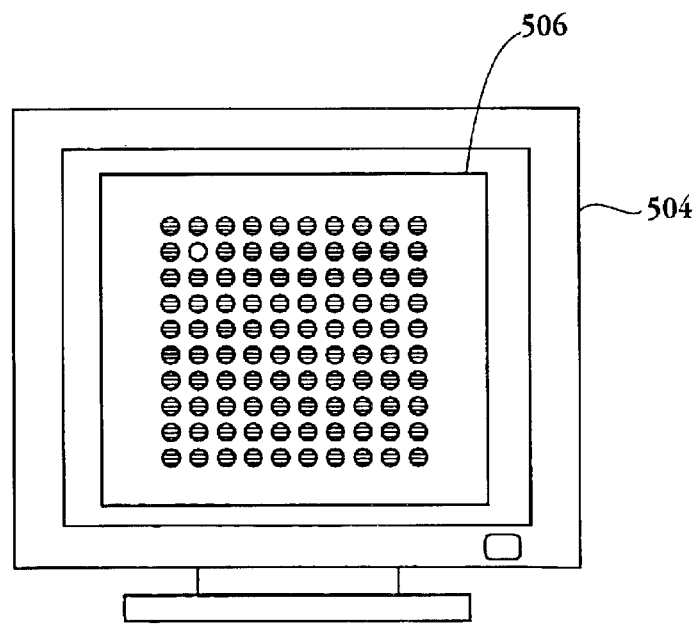
FIG. 8C is a schematic view of a display device, which may be used in connection with the cameras shown in FIG. 8B, for displaying an image of the lower end of a projection array.

In another exemplary arrangement, illustrated in FIGS. 8B and 8C, the means for determining the presence or absence of a target object, such as a bead, at the lower end region of each projection includes one or more cameras or other suitable image capture devices positioned below, but in substantially vertical alignment with, the arcuate or circular path in which extractors 50a and 50b and corresponding projection arrays 56a and 56b travel between the "picking up" and "releasing" steps.

In the illustrated embodiment, where two extractors are employed, two cameras 500a and 500b can be used. In this embodiment, after extractor 50a and its projection array 56a executes a bead "pick up" operation in the position denoted by the letter A and after extractor 50b and its projection array 56b executes a bead "release" operation in position C, the rotation motor 64 is controlled to rotate extractors 50a and 50b to positions B and D, respectively, where the extractors are temporarily held while the individual projections of corresponding projection arrays 56a and 56b are checked for the presence or absence of beads. When in position B, the lower end of projection array 56a is positioned above, and in the field of view of, a lens 502a of camera 500a which captures an image 506 of the lower end, depicting the ends of all of the individual projections, preferably as seen along the axis of the projections. As shown in FIG. 8C, the image is transmitted to a suitable display device 504 such as CRT or LCD display where the image is displayed to enable an operator to visually determine if any projection failed to pick up a bead, or if any projection picked up more than one bead. Similarly, when in position D, the lower end of projection array 56b is in the field of view of a lens 502b of camera 500b. In this case, the image captured by camera 500b and displayed on the monitor is used to determine if any projection of projection array 56b failed to release a bead. By looking at the exemplary image 506 on the display device in FIG. 8C it can easily be seen that that each of the projections, except the one in row 2, column 2 contain a bead. It should be noted that the display device may be part of the image capture device, or may be a separate unit in communication therewith.

If the check step performed with cameras 500a and 500b reveals that any projection of projection array 56a failed to pick up a bead in position A, or that any projection of projection array 56b failed to release a bead in position C, rotation motor 64 is controlled to rotate extractors 50a and 50b back to positions A and C, respectively, where the corresponding pick up and/or release step is again executed, as required. Afterward, projection arrays 56a and 56b are again rotated to positions B and D, respectively, where they are once again checked for the presence or absence of beads by cameras 500a and 500b before continuing to positions C and A, respectively.

Although, in the illustrated embodiment, each camera is positioned about 90° between the pick up and release positions, this is not necessary. It should be appreciated that the cameras may be positioned at other locations along the arcuate travel path. For example, one camera may be offset 45° in the counterclockwise direction from position A while the other camera is offset the same degree in the same direction relative to position C.

It should also be appreciated that more or less than two cameras may be employed, depending on the number of extractors used. For example, in another embodiment of the invention where only a single extractor is used, only a single camera, located at either position B or D, need be used. In this case, the extractor will move back and forth along an arcuate path defined by either ABC or ADC, depending on where the camera is located. Thus, the single camera will perform both the check after pick up and the check after release. In other embodiments, where three or more extractors are used, two or more cameras may be employed.

As previously mentioned, the attracted and retained beads can be moved to a deposit position whereat the beads can be released. In one embodiment, for example, the deposit location is over a substrate, such as a micro-plate or card, having a plurality of bead-receiving locations. FIG. 1 shows, for example, a substrate, denoted as 122, having a plurality of spaced-apart wells, such as 124a–12f, for receiving and holding beads.

The receiving wells of substrate 122 can be configured for alignment with the projections 54a–5f, 54g–54l of projection arrays 56a, 56b. In this regard, wells 124a–124f can be formed with the same center-to-center spacing as projections 54a–5f, 54g–54l. In one particular embodiment, a bead-receiving substrate is provided as an injection-molded plate, or tray, made of any suitable material, such as acrylic, polycarbonate, polypropylene, polysulfone, or the like. Preferably, the length and width of the tray conform to the commonly used standard of 5.03"×3.37" (127.8 mm and 85.5 mm), although other outer dimensions can be used. A regular array of depressions, or wells, are provided in the tray for separately receiving and holding reagent beads dropped from above. For example, the instant embodiment contemplates a 16×24 array of wells integrally formed with the tray, with adjacent wells spaced apart about 4.50 mm center-to-center. Each well, in this embodiment, has an interior region, or lumen, that is substantially square in horizontal cross-section, and a bottom or floor region that is generally flat. It should be appreciated, however, that wells of any desired geometrical configuration (e.g., oval, square, rectangular, triangular, etc.) can be used. Similarly, the wells may be of any desired shape when viewed along their longitudinal axes, e.g., straight, tapered or other shape. For the square wells of the present embodiment, the four sidewalls of each well are provided with a slight inward taper (i.e., the distance between opposing sidewalls continuously decreases) along the direction extending from the well's upper, receiving end toward the floor region. Preferred dimensions for each well in this embodiment are as follows: (i) about 1 mm in depth (top to bottom); (ii) about 1 mm×1 mm across an uppermost opening; and (iii) about 0.50 mm×0.50 mm across a flat, bottom floor region.

The depending projections of an extractor, intended for use with the just-described tray, can similarly be arranged in a 16×24 array, with adjacent projections spaced apart about 4.50 mm center-to-center. By this construction, the extractor can be positioned over the 16×24 array of wells in the tray, with the two arrays in alignment. In use, a plurality of beads retained by the extractor can be deposited directly into the wells of the tray. For example, a plurality of retained beads on such a projection array can be lowered into close proximity with respective openings of the well array. From this position, the beads can be released from the projections, in a substantially simultaneous fashion, so that each bead falls into a respective well.

In another embodiment, a generally square micro-card, about 1"×1", is provided with a 32×32 array of wells. As with the previous embodiment, each well of the array is formed with a substantially square horizontal cross-section, and a generally flat bottom or floor region. Again, it should be noted that other well configurations can be used. Preferred dimensions for each well, according to this embodiment, are as follows: (i) about 1 mm in depth (top to bottom); (ii) about 0.60 mm×0.60 mm across an uppermost opening; and (iii) about 0.35 mm×0.35 mm across a bottom floor region. Downwardly convergent (tapered) sidewalls extend between the top opening and floor of each well. Adjacent wells in the array are spaced about 1–2 mm apart (center-to-center), and preferably about 1.50 mm. So constructed, each well can hold, for example, up to three substantially spherical reagent beads, each having a diameter of between about 275–325 micrometers, and preferably about 300 micrometers.

An extractor, suitable for use with the just-described micro-card, can be provided with an array of projections disposed in an array that is complementary to the array of wells in the card, permitting direct alignment of each of the projection arrays with the array of wells.

Instead of depositing the beads directly onto a substrate, as described above, one embodiment provides a means for guiding or channeling each bead, once released from a projection end region, to a respective receiving location on the substrate. Such means can include, for example, a conduit or channel assembly adapted for positioning between the projection array and substrate. Referring to the embodiment of FIG. 1, for example, a conduit assembly, indicated generally at 126, includes a plurality of conduits 128a–128f in a support structure 130. Support structure 130 maintains the conduits in fixed, spaced relation to one another. In one embodiment, the support structure takes the form of a frame, or rack, into which individual conduits can be secured (e.g., snap fit). In another embodiment, the conduits are integrally formed with the support structure. For example, the conduit assembly can be constructed of plastic using an injection molding process; or each conduit can be formed by boring through a block of material, such as glass, plastic, metal, or the like.

The top of conduit assembly 126 is provided with an array of openings for receiving beads that have been released from a projection array, such as 56a or 56b. In a preferred embodiment, the conduit upper-opening array is configured for alignment with each of the projection arrays. In this regard, the upper openings of conduit assembly 126 and the projections 54a–5f, 54g–54l of each projection array 56a, 56b can be arranged with substantially the same pitch (center-to-center spacing). The bottom of conduit assembly 126 provides an array of openings through which beads can egress. The conduit lower-opening array can be configured for alignment with the array of wells of the substrate. For example, the openings at the bottom of conduit assembly 126 and the wells 124a–124f of substrate 122 can be formed with substantially the same pitch.

In order to facilitate passing of a released bead from a projection end region down into a conduit positioned thereunder (i.e., ease the tolerance of bead delivery by the extractor), the upper end of each conduit 128a–128f can be formed with an expanded, or enlarged-diameter, opening. In one embodiment, for example, each conduit upper opening is at least 150%, and preferably greater than 250%, the size of an opening defined by the lower rim or lip of a respective projection end region. To facilitate passing of a bead from a conduit down into a respective well of a bead-receiving substrate, the lower opening of each conduit can be formed with a diameter that is generally no larger than the upper opening of a respective receiving well. In a preferred embodiment, the lower opening of each conduit 128a–128f is smaller than the upper opening of a respective receiving well 124a–12f. In an exemplary construction, each conduit lower opening is between about 40–95%, and preferably about 70%, the size of the opening of a respective receiving well. For example, a generally circular lower opening of a conduit, having a diameter of about 400 micrometers, can be positioned over a substantially square receiving well having an upper opening measuring about 600×600 micrometers.

From the above discussion, it should be appreciated that it will often be advantageous to utilize a conduit assembly wherein each conduit has a large upper opening and a small lower opening (relative to one another). In one embodiment, for example, each conduit upper opening has a diameter of between about 1 mm–10 mm, and each lower opening has a diameter of less than 1 mm. In one particular construction, each large opening has a diameter of between about 1–6 mm; and preferably about 2 mm; and each small opening has a diameter of between about 0.25–0.75 mm, and preferably about 0.40 mm.

With continuing reference to FIG. 1, between its upper and lower ends, each conduit 128a–128f of conduit assembly 126 can be shaped to promote ready passage of a bead therethrough and down onto a substrate, such as 122, thereunder. One embodiment, for example, provides downwardly convergent (tapered) sidewalls between the upper and lower openings of each conduit. In the exemplary arrangement of FIG. 1, the sidewalls of each conduit are generally straight along the longitudinal direction, defining generally cone-shaped conduits. In another exemplary arrangement, the sidewalls are curved along the longitudinal direction, defining generally horn-shaped conduits.

As previously indicated, it is often advantageous to utilize a conduit assembly having an upper-opening array configured with substantially the same pitch as the projection array, and further having a lower-opening array configured with substantially the same pitch as the receiving-well array of a substrate. Thus, in systems where the pitch of both the projection and receiving-well arrays are substantially the same, the pitch of the conduit upper- and lower-opening arrays will be about equal. For example, FIG. 1 shows an embodiment wherein each of (i) the projection arrays, (ii) the receiving-well array, and (iii) the conduit upper- and lower-opening arrays all have substantially the same center-to-center spacing.

Figure 9:
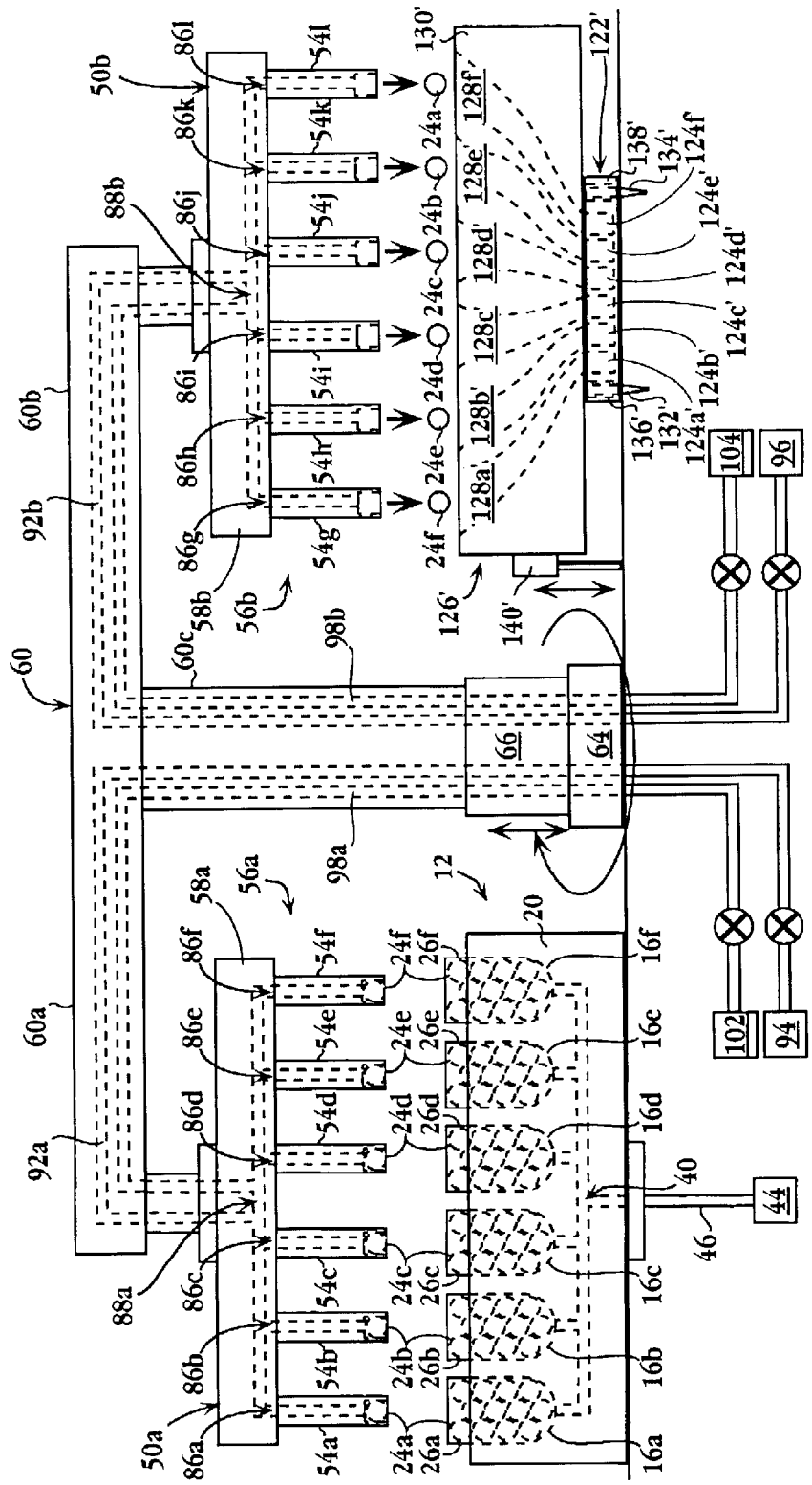
FIG. 9 is a partially schematic side elevational view, with portions shown in phantom, of a system for fabricating a micro-array of reagent-carrying beads on a substrate, constructed in accordance with an embodiment of the present invention.

In systems where the pitch of the projection and receiving-well arrays differ, on the other hand, it will often be advantageous to utilize a conduit assembly having upper- and lower-opening arrays that differ in pitch, as well. In one exemplary system of this type, the conduit lower-opening array is provided with a center-to-center pitch that is smaller than that of the conduit upper-opening array. FIG. 9 shows, for example, an embodiment much like that of FIG. 1, except that receiving wells 124a'–124f' of substrate 122' are arranged in an array having a pitch that is substantially smaller than that of the projection arrays 56a, 56b. Consequently, the upper- and lower-opening arrays of conduit assembly 126', in this embodiment, differ in pitch in a similar fashion. For example, the center-to-center pitch of the lower-opening array can be between about ½ to ¼ that of the upper-opening array. In one particular embodiment, the center-to-center pitch of the lower-opening array is about ⅓ that of the upper-opening array.

Figure 10A:
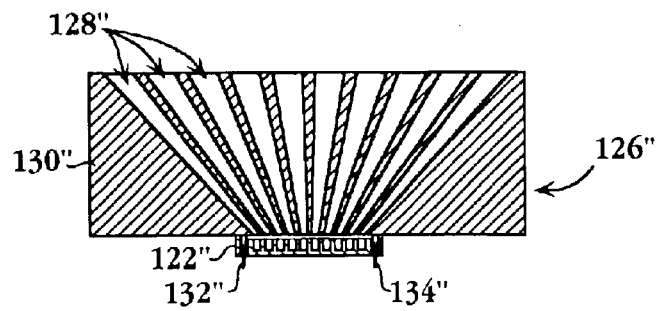
FIG. 10(A) is a side cross-sectional view of a conduit assembly having an array of conduits configured for separately directing a plurality of beads into the wells of a micro-plate or card, in accordance with an embodiment of the present invention.
Figure 10B:
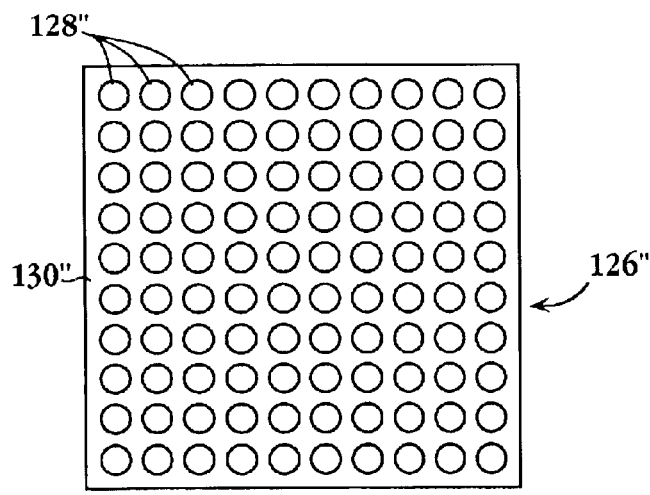
FIG. 10(B) is a top plan view of the conduit assembly of FIG. 10(A), showing an array of large openings of the conduits.
Figure 10C:
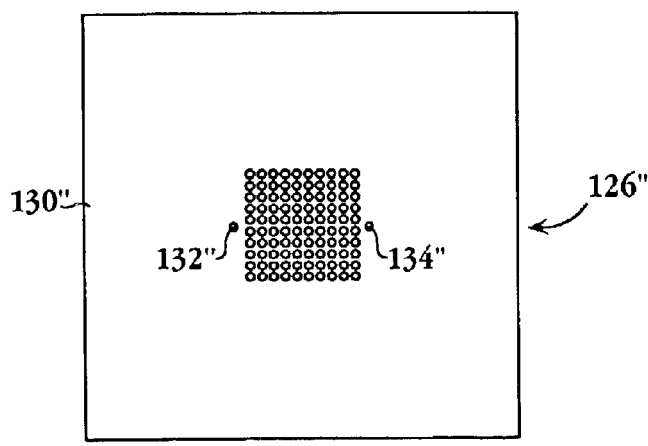
FIG. 10(C) is a plan view from beneath the conduit assembly of FIG. 10(A), showing an array of small openings of the conduits, as well as a pair of indexing pins on either side of the small-opening array.

With further regard to shape, it should be noted that each of conduits 128a'–128f' of FIG. 9 is curved along its longitudinal direction such that it roughly defines an "S" shape. In another embodiment, one or more of the conduits are substantially straight. In this regard, attention is drawn to conduit assembly 126" of FIGS. 10(A)–10(C). In this arrangement, a 10×10 array of conduits, such as at 128", are formed in a support structure, such as block 130". Block 130", in turn, is situated over a micro-card 122" having a 10×10 array of receiving wells that are aligned with the conduit assembly's lower-opening array. The conduit assembly's upper-opening array, as depicted in FIG. 10(B), can have, for example, 4 mm diameter openings disposed at a 6mm pitch, and the lower-opening array, shown in FIG. 10(C) can have 0.4 mm diameter openings disposed at a 1.5 mm pitch.

The conduit assembly can be manually placed over the bead-receiving substrate, or it can be placed over the substrate in an automated fashion. In either case, it will often be helpful to include in the system a means for registering the bead-receiving locations of the substrate with the lower-opening array of the conduit assembly. In one embodiment, indexing pins, such as at 132,134 in FIG. 1, depending from the lower side of conduit assembly 126, can assist in registering the wells of micro-plate 122 with the lower-opening array of conduit assembly 126. Particularly, each indexing pin 132, 134 is alignable with a respective indexing bore, such as 136, 138, formed through a corresponding region of substrate 122. Insertion of the indexing pins in the indexing bores substantially aligns the lower-opening array of the conduit assembly with the array of wells of the micro-card.

With further regard to placement of the conduit assembly over a substrate, one embodiment contemplates the inclusion of a conventional motor or pneumatic lifter in the system, such as at 140 and 140' in FIGS. 1 and 9, respectively. Lifter 140 is adapted to raise and lower the conduit array along a generally vertical pathway. Those skilled in the art can readily select a suitable lifter from the devices that are available from commercial sources. Preferably, lifter 140 is adapted for operation under the direction of a control computer (not shown).

Figure 11:
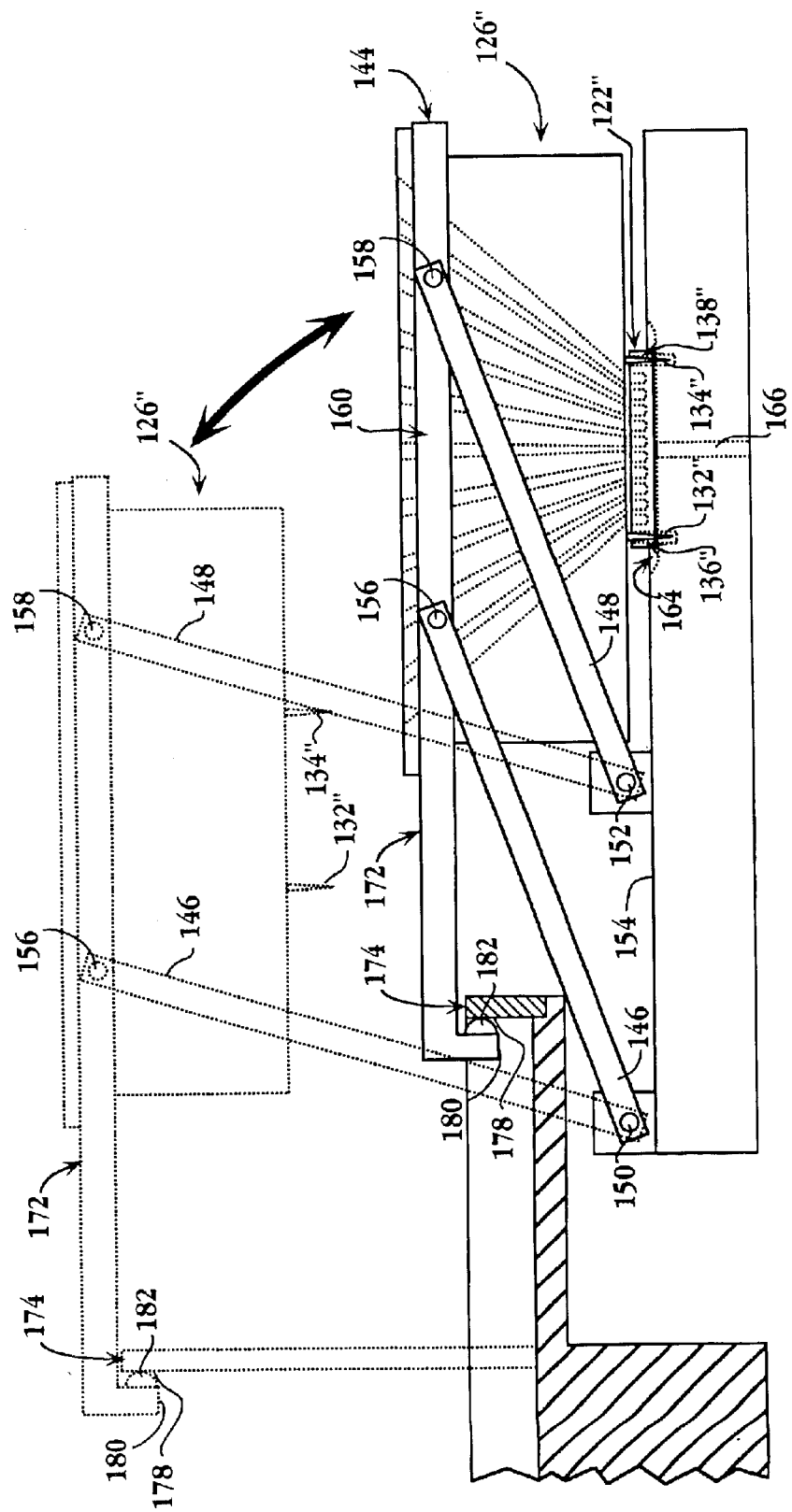
FIG. 11 is a partially schematic side elevational view, with portions depicted in phantom, of a parallelogram linkage assembly for reciprocally moving a conduit assembly between a raised position, shown in dashed lines, and a lowered position over a bead-receiving substrate, shown in solid lines, in accordance with an embodiment of the present invention.

In another embodiment, a parallelogram linkage assembly supports a conduit assembly for reciprocal movement between a raised position and a lowered position. FIG. 11, for example, shows an exemplary parallelogram linkage assembly, indicated generally as 144, supporting conduit assembly 126" for such movement. In the illustrated arrangement, first and second side links, denoted respectively as 146 and 148, are provided along one side of linkage assembly 144. The lower ends of side links 146, 148 are pivotally attached at respective, spaced-apart locations, or pivot points, 150, 152 proximate a supportive surface 154, and pivotally attached at their upper ends, in a similarly spaced-apart fashion, at pivot points 156, 158 along a horizontal link 160. By this construction, horizontal link 160 can be moved up and down along a generally arcuate pathway between a raised position, as depicted in broken lines, and a lowered position, as shown in solid lines. Although not visible in FIG. 11, an additional pair of side links, like side links 146 and 148, are provided on the opposite side of linkage assembly 144. A substrate holding area, indicated generally as 164, is provided adjacent to parallelogram linkage assembly 144 for receiving and holding a bead-receiving substrate, such as 122". Conduit assembly 126" becomes positioned over substrate 122" when linkage assembly 144 is at its lowered position (solid lines).

Figure 12A:
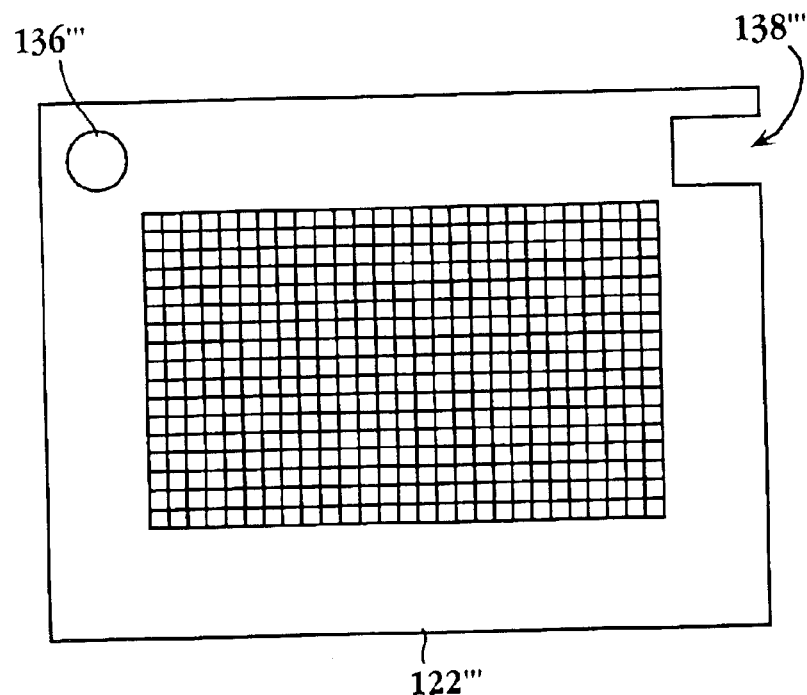
FIG. 12(A) is a top plan view of a multi-well micro-card having an indexing bore formed along one side and an indexing slot formed along an opposing side, according to the teachings of the present invention.
Figure 12B:
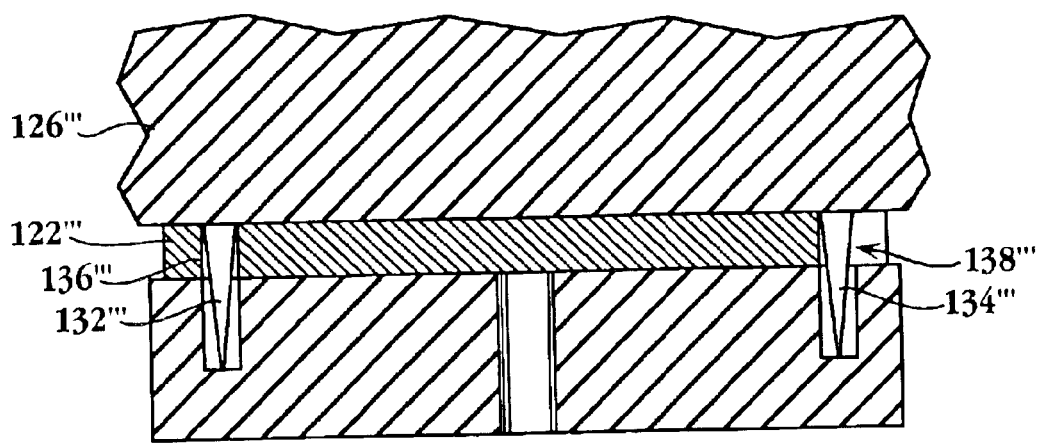
FIG. 12(B) shows, in side-sectional view, the multi-well card of FIG. 12(A) resting on a substrate-holding area, and a pair of indexing pins extending from a conduit assembly passed through the bore and slot of the card, in accordance with an embodiment of the present invention.

Indexing pins 132", 134" are adapted to mate with respective indexing bores 136", 138" in substrate 122" to assist in aligning the lower-opening array of conduit assembly 126" with the well array of substrate 122". Details of a similar indexing arrangement are shown in FIGS. 12(A)–12(B). Here, one indexing pin, such as 132'", can be aligned with a bore 136'" through micro-card 122'", and a second pin 134'" can be aligned with slot 138'" formed in micro-card 122'". Returning to the view of FIG. 11, a passageway 166 can open into a central region of the substrate holding area 164. By connecting conduit 166 to a remote pressure-control source, a vacuum can be established reaching to, and drawing upon, the lower surface of a bead-receiving substrate 122", thereby maintaining the substrate in a seated position.

It should be noted that there are other ways of positioning the conduit assembly relative to the micro-card. For example, a linear arrangement of two motors may be used. In this arrangement, one motor can be used to move the conduit assembly into place over the micro-card. The other motor can then be used to push the micro-card into the conduit assembly to connect them after the conduit assembly has been moved into place.

Figure 13:
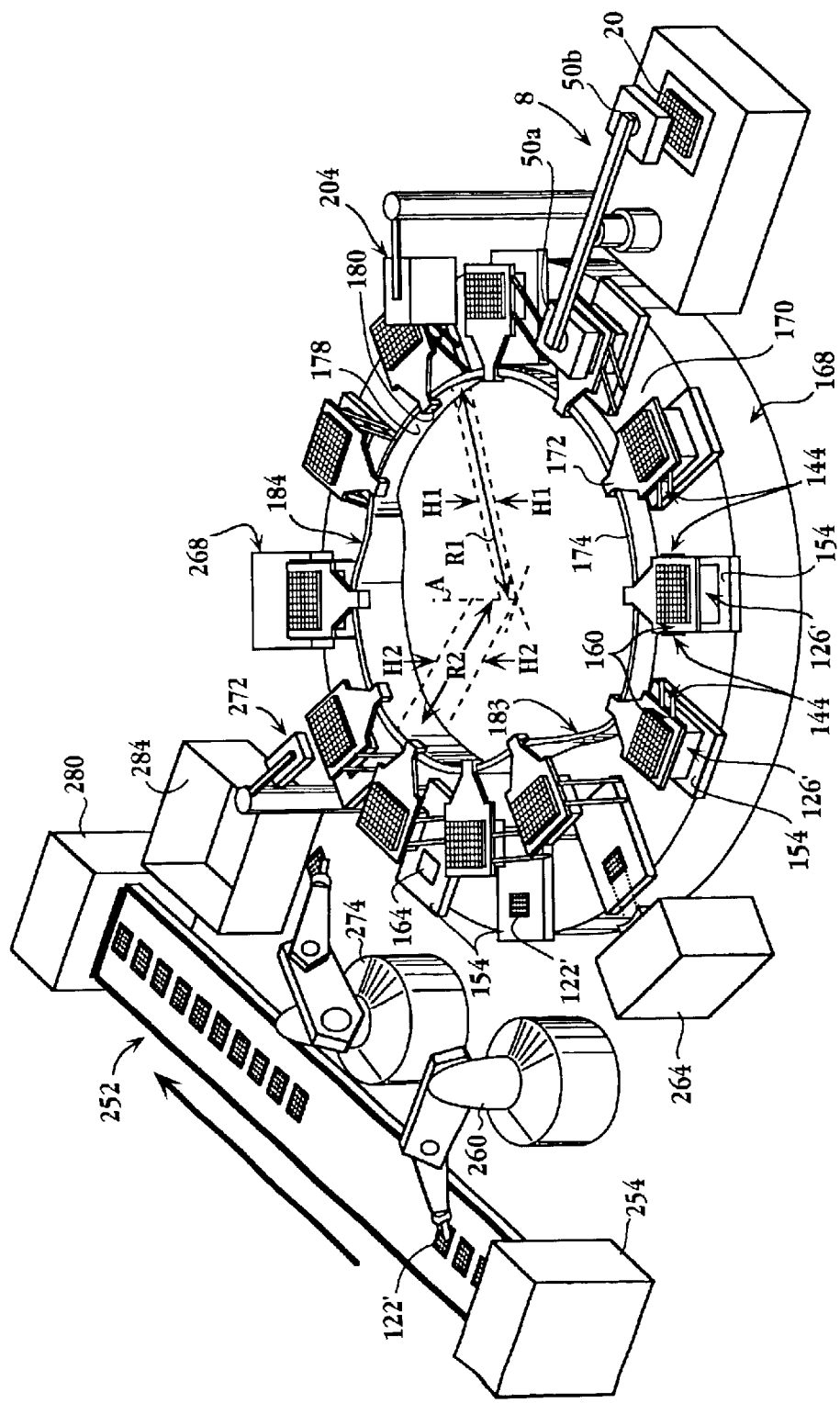
FIG. 13 is a perspective view of a high-throughput system for fabricating an array of beads on a micro-plate or card, according to one preferred embodiment of the present invention.

With additional reference to the perspective view of FIG. 13, a plurality of parallelogram linkage assemblies, such as 144, each carrying a respective conduit assembly 126', can be seen in combination with a carousel arrangement, denoted generally as 168. Rotational motion of carousel 168 causes the various linkage assemblies to revolve about the carousel's central axis "A". Preferably, such motion of the carousel is carried out under the direction of a control computer (not shown). Each conduit assembly is disposed along a region of a respective horizontal link 160 lying radially outward of axis "A". In one embodiment, for example, each horizontal link is rigidly attached to, or integrally formed with, a frame structure having a central opening (not visible in FIG. 13) configured to receive and support a respective conduit assembly. The other end of each horizontal link 160 rigidly attaches to, or is integrally formed with, an elongated arm 172 that extends in the direction of the carousel's rotational axis "A," reaching to and engaging a rail 174 running along the inner region of the carousel's supportive surface. As best seen in FIG. 11, rail 174 provides a bearing surface 178, further described below, along which each linkage assembly 144 can ride as it is advanced by carousel 168. In this regard, elongated arm 172 includes a downwardly angled, terminal bend 180 adapted to slide along bearing surface 178. A bearing material can be attached to bend 180 along a region confronting bearing surface 178. Preferably, the bearing material is selected to provide a contact interface with low sliding friction. For example, FIG. 11 illustrates a boss 182 formed of a low-friction material, such as polytetrafluroethylene (PTFE) or the like, bonded to bend 180 at a region adjacent bearing surface 178.

As mentioned above, and with particular reference to the perspective view of FIG. 13, it can be seen that rail 174 runs along an inner region of the carousel's supportive surface 170. More particularly, the bearing surface 178 of rail 174 includes (i) a first arcuate section disposed a first distance R1 from rotational axis "A" at a first vertical height H1 above the carousel's supportive surface; and (ii) a second arcuate section disposed a second distance R2 from axis "A," shorter than distance R1, at a second vertical height H2, higher than vertical height H1. The configuration of each such arcuate section is nearly that of a semicircle, measuring between about 60–85 degrees. Transition sections, as at 183 and 184, bridge the first and second arcuate sections. Together, the first and second arcuate sections, and the transition sections, provide a continuous, bearing surface, appearing roughly oblong in top plan view (not shown).

In operation, as each parallelogram linkage assembly 144 is advanced along the first arcuate section of rail 174, a respective conduit assembly 126' will be located at the lowered position, directly over a substrate 122'. As each parallelogram linkage assembly is moved along the second arcuate section, its respective conduit assembly will locate at the raised position, above and offset from the substrate.

Detection instrumentation can be included in the system of the invention for determining the presence of a bead at target locations of a bead-receiving substrate, such as in the wells of a micro-card. In one embodiment, all beads carrying a particular reagent are formed to display a unique, pre-assigned color. The detection instrumentation, in this embodiment, is adapted to inspect each target well for a bead of such color. In the exemplary arrangement of FIG. 14, an illumination source, such as laser 186, directs an expanding radiation beam 188 towards a lens 190. Lens 190 focuses the beam to irradiate the upper-opening array of conduit assembly 126" so that a fraction of the beam passes down through each conduit to the wells of plate 122". Upon striking each well, and its contents (if any), a retro-beam 192 of reflected light travels back up through each conduit, towards lens 190. To facilitate passage of the retro-beam through the conduits, each conduit can have a reflective inner surface, e.g., a highly polished metallic surface. Lens 190 focuses the retro-beam 192 to pass through an aperture 193 and fall upon a collimating lens 194 which, in turn, directs the beam to a color filter 196. Color filter 196 only permits light of a designated wavelength (or range) to pass to a sensor array of an adjacent camera device, such as CCD camera 198. Each well of micro-card 122" is assigned to one or a few photo-detectors of the CCD camera 198. Target wells that have been successfully loaded with a bead of the designated color will provide a retro-beam capable of passing through the color filter and striking respective photo-detectors of the CCD camera. The photo-detectors, in turn, can communicate an output signal for visualization on a video screen and/or transmission via an appropriate interface to a computer. In either case, a positive signal is indicative of successful loading. Any target well(s) failing to hold a bead of the designated color, on the other hand, will not be able to generate a retro-beam capable of reaching the CCD camera. Accordingly, the photo-detector(s) assigned to such well(s) will not produce a signal and a loading failure is indicated. A new loading attempt can then be made, or the card can be rejected.

Rather than relying only upon reflected light to provide a retro-beam from each well, the coating on each bead can be of a type that fluoresces upon being illuminated with light of a certain wavelength. In this way, each bead can generate fluorescent emissions of a particular, pre-assigned color indicative of the reagent that it carries.

Figure 14:
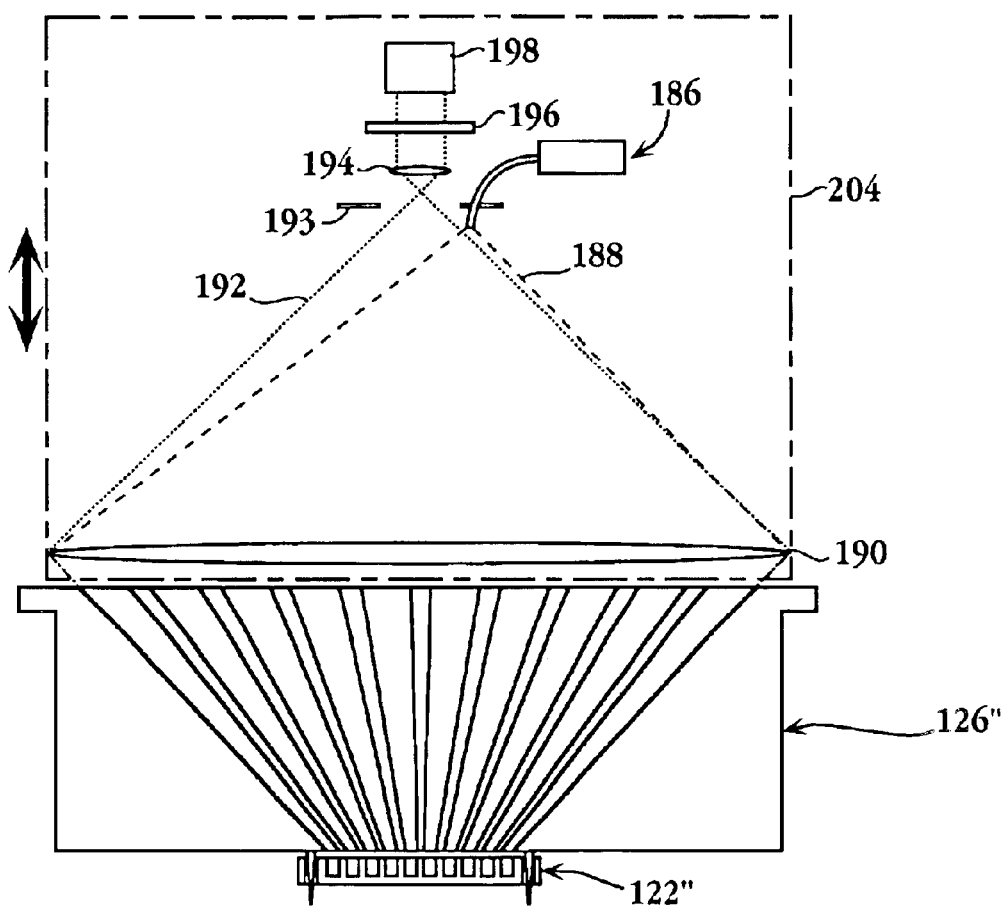
FIG. 14 is a partially schematic side-sectional view of a detection system for determining the presence of beads at bead-receiving locations of a substrate, in accordance with an embodiment of the present invention.
Figure 15:
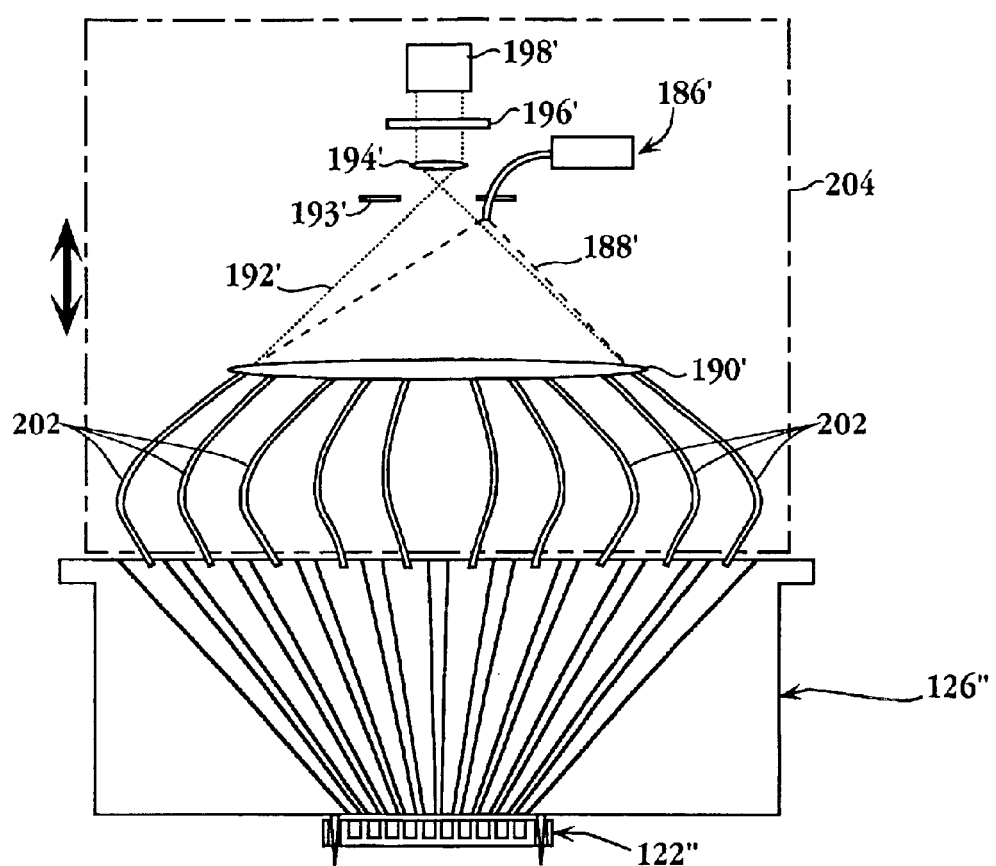
FIG. 15 is a partially schematic side-sectional view of a detection system, similar to that of FIG. 14, further including an array of optical fibers configured to extend down into the conduits of a conduit assembly positioned over a bead-receiving substrate, according to a further embodiment of the present invention.

In another embodiment, similar to that of FIG. 14 (described above), an array of optical fibers communicates an illuminating beam with a plurality of target locations of a bead-receiving substrate, and further communicates a retro-beam leaving each target location with a light-sensitive camera device. As shown in FIG. 15, for example, an expanding beam 188' emanating from laser a 186' is directed through a lens 190' onto the terminal ends of an array of optical fibers, including fibers 202. The other terminal end of each fiber is disposed above, or in, a respective conduit of conduit assembly 126". In one particular arrangement, each fiber extends down through a respective conduit to a location slightly above a respective bead-receiving well. A retro-beam, leaving each well, can travel up through its respective fiber towards lens 190'. Lens 190' focuses the retro-beam 192' to pass through an aperture 193' and fall upon a collimating lens 194' that, in turn, directs the beam to a color filter 196'. As with the previous embodiment, color filter 196' only permits light of a designated wavelength (or range) to pass to a sensor array of an adjacent camera device, such as CCD camera 198'. Additional details are substantially like those of the previous embodiment.

In certain applications, it may be desirable to detect beads of different colors, e.g., blue beads, red beads and green beads. To this end, either of the above-described detection assemblies (FIGS. 14 and 15) can be provided with a plurality of color filters, with each filter being independently movable in and out of the retro-beam path prior to the camera device. By selecting an appropriate filter, and moving it into position for interception of the retro-beam, beads of a particular color can be detected. Another embodiment contemplates the use of multiple, separate detection assemblies, each being configured to detect beads of a particular color. The detection assemblies can be substantially alike, except that each includes a uniquely colored filter. For example, one detection assembly can include a filter adapted for the detection of blue beads, another can include a filter for detecting red beads, and a third can have a filter for detecting green beads. The different detection assemblies can be arranged in series along a conveyor apparatus carrying bead-receiving substrates.

The broken-line rectangle 204 surrounding certain of the detection assembly components in FIGS. 14 and 15 schematically represents a housing or case within which the detection assembly components can be mounted. In one preferred embodiment, the housing is adapted for reciprocal linear movement along a generally vertical pathway over a conduit assembly. With particular reference to the embodiment of FIG. 15, for example, laser 186', lenses 190' and 194', aperture 193', color filter 196' and CCD camera 198' can all be mounted in housing 204. The upper region of each optical fiber 202 is also mounted in the housing, with the terminal end of each fiber facing lens 190'. The lower ends of the optical fibers project out through the bottom wall of housing 204. The projecting fiber ends are arranged in an array complementary to the conduit upper-opening array. By this construction, the detection assembly can be lowered over a conduit assembly and micro-card, such as 126" and 122", in a fashion permitting each fiber end to enter, and extend down into, a respective conduit. Once the detection has been completed, the detection assembly can be raised and another conduit assembly/micro-card can be moved into position under the detection assembly.

Instead of inspecting for the presence of beads in the wells of a substrate while a conduit assembly is lowered thereover, as described above, one embodiment contemplates removal (lifting) of the conduit assembly prior to detection. In this embodiment, the detection assembly irradiates the wells directly, and detects for the presence of beads on the basis of color.

Another feature of the present invention provides a system for covering an array of wells formed in a substrate, such as a micro-plate or card. According to one embodiment, depicted in the side-sectional view of FIG. 16(A), the system includes a continuous web of a cover material, denoted as 212, mounted for movement from a supply position, such as idler reel 214, to a take-up position, such as driven reel 216. Shearing blades 218 are mounted on the lower face of a movable piston 222 for reciprocal linear motion along a direction substantially normal to the web for cutting out a portion of the cover material 212 at a region between the supply position 214 and take-up position 216. A resiliently compliant, generally planar surface, indicated at 220, is provided on the lower face of piston 222 along a region between blades 218 for pressing the cover material against the upper surface of a substrate, such as micro-card 122".

Figure 16A:
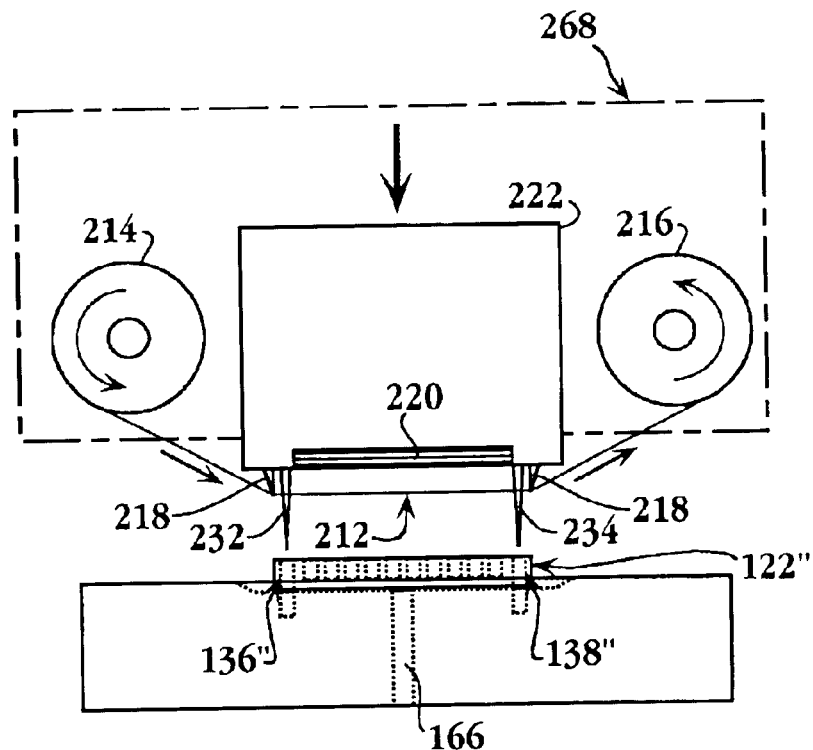
FIG. 16(A) is a partially schematic side-sectional view of a system for covering an array of wells formed in a substrate, such as a micro-plate or card, with a film-like cover material, according to an embodiment of the present invention.
Figure 16B:
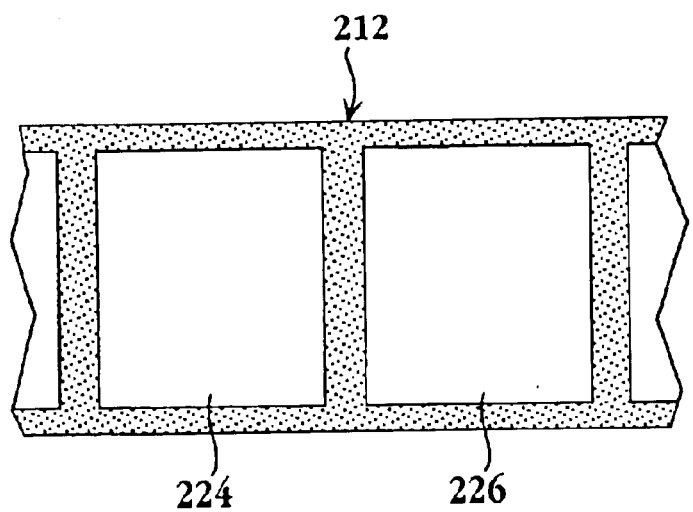
FIG. 16(B) is a top plan view of a length of cover material on a take-up reel of the device of FIG. 16(A), showing areas that have been cut out for use in covering the wells of substrates, in accordance with the teachings of the present invention.

Indexing pins 232, 234, depending from the lower face of piston 222, can register with indexing bores 136", 138" of the substrate 122" to orient the shearing blade 218 thereover for effecting a desired cut in web 212. Although not visible in the sectional view of FIG. 16(A), the shearing blades collectively provide a cutting edge defining a quadrilateral, such as a square or rectangle. In this regard, FIG. 16(B) illustrates sequential cuts 224, 226 made in web 212 by shearing blades 218, with each cut having (i) two sides substantially parallel to the side edges of the web and (ii) two sides substantially normal to the side edges of the web.

Any suitable cover material can be utilized. Preferred materials are substantially chemically inert with the reagents placed in the wells. One embodiment contemplates the use of a cover material that is capable of forming a substantially fluid-tight seal with the upper surface of a multi-well tray, or appropriate regions thereof (e.g., an upstanding rim or lip about the opening of each well). Such a seal can be effected, for example, using conventional adhesives and/or heat sealing techniques. Suitable heat-sealable materials include, for example, polymeric films, such as polystyrene, polyester, polypropylene and/or polyethylene films. Such materials are available commercially, for example, from Polyfiltronics, Inc. (Rockland, Mass.) and Advanced Biotechnologies (Epsom, Surrey England UK). One embodiment contemplates the use of a substantially clear polymeric film, e.g., between about 0.05–0.50 millimeters thick, that permits optical measurement of reactions taking place in the covered wells. In this regard, it will be recalled that the present invention contemplates real time fluorescence-based measurements of nucleic acid amplification products (such as PCR). Generally, in such a technique, an excitation beam is directed through a sealing cover sheet into each of a plurality of fluorescent mixtures separately contained in an array of reaction wells, wherein the beam has appropriate energy to excite the fluorescent centers in each mixture. Measurement of the fluorescence intensity indicates, in real time, the progress of each reaction. For purposes of permitting such real time monitoring, each sheet in this embodiment is formed of a heat-sealable material that is transparent, or at least transparent at the excitation and measurement wavelength(s). One suitable heat-sealable sheet, in this regard, is a co-laminate of polypropylene and polyethylene. A heatable platen (not shown) can be used to engage the sheet, once cut and placed over an array of wells, and to apply heat so that the sheet bonds to the substrate.

At this point, attention is directed to the perspective view of FIG. 13, wherein a number of the above-described features of the invention can be seen embodied in a high-throughput system for fabricating an array of beads on a micro-plate or card. Generally, a linear conveyor 252 transports, in serial fashion, empty micro-cards 122' from a supply area 254 to a position adjacent a first robot 260. As the robot 260 picks up an empty card 122' from the conveyor 252, a rotatable carousel 168 advances a platform 154 and an associated, movable conduit assembly 126' to a location also adjacent the robot 260. Notably, the conduit assembly 126' is disposed at a raised position, above and vertically offset from a substrate-holding area 164 of the platform 154. The robot 260 places the card 122' at the unoccupied substrate-holding area 164, and the carousel 168 rotates to advance the card 122' to a position adjacent a scanning assembly 264. With the conduit assembly 126' still raised, the scanning assembly 264, e.g., a bar-code reader, scans a label on the side of the card 122'. This operation can serve, for example, to ensure that the card has been properly placed at the substrate-holding area and to read identifying information into a control computer (not shown). Next, a parallelogram linkage assembly 144 lowers the conduit assembly 126' to a position directly over the card 122', with a lower-opening array of the conduit assembly 126' aligned with a complementary array of wells in the card 122'. The card 122' is then advanced to a loading position adjacent a bead dispensing arrangement, as at 8, which can be constructed substantially as shown in FIG. 9. The dispensing arrangement 8 is operable to pick up a plurality of beads from a reagent plate 20 and, upon rotating about 180°, to deposit the beads into the micro-card 122' via the conduit assembly 126', as previously described. Further regarding the dispensing arrangement 8, it should be appreciated that while one bead extractor 50a deposits a set of beads into the wells of a micro-card, the other extractor 50b can simultaneously pick up another set of beads from the reagent plate 20 for placement in the next card advanced to the loading position. This operation can continue until all of the empty cards have been filled and/or the supply of reagent beads has been exhausted.

Having received beads from the dispensing arrangement 8, the card 122' is then advanced to a position below a detection assembly 204, e.g., like that of FIG. 15 that inspects each well of the card 122' for the presence of a bead. As the card 122' leaves the detection assembly 204, the conduit assembly 126' is returned to the raised position, and the card 122' is presented to a sealer 268 that places a cover, such as an optically clear membrane, over the wells. The sealer can be constructed, for example, substantially as shown in FIG. 16(A). A second camera, as at 272, then inspects the card 122' to ensure proper placement of the cover. Finally, the card 122' is advanced to a second robot 274, located between the carousel 168 and conveyor 252, which lifts the card 122' from the substrate-holding area 164. If the inspection operations indicate that the card 122' has been properly loaded with beads and effectively sealed, the card 122' is then placed back on the linear conveyor 252 and transported to a storage location 280. If a failure in either of these regards has been indicated, on the other hand, the robot 274 can instead deposit the card 122' in a reject bin, as at 284.

A control computer (not shown) can integrate the operation of the various assemblies, for example through a program written in an event driven language such as LABVIEW® or LABWINDOWS® (National Instruments Corp., Austin, Tex.). In particular, the LABVIEW software provides a high level graphical programming environment for controlling instruments. U.S. Pat. Nos. 4,901,221; 4,914,568; 5,291,587; 5,301,301; 5,301,336; and 5,481,741 (each expressly incorporated herein by reference) disclose various aspects of the LABVIEW graphical programming and development system. The graphical programming environment disclosed in these patents allows a user to define programs or routines by block diagrams, or "virtual instruments." As this is done, machine language instructions are automatically constructed which characterize an execution procedure corresponding to the displayed procedure. Interface cards for communicating the computer with the motor controllers are also available commercially, e.g., from National Instruments Corp.

Figure 17A:
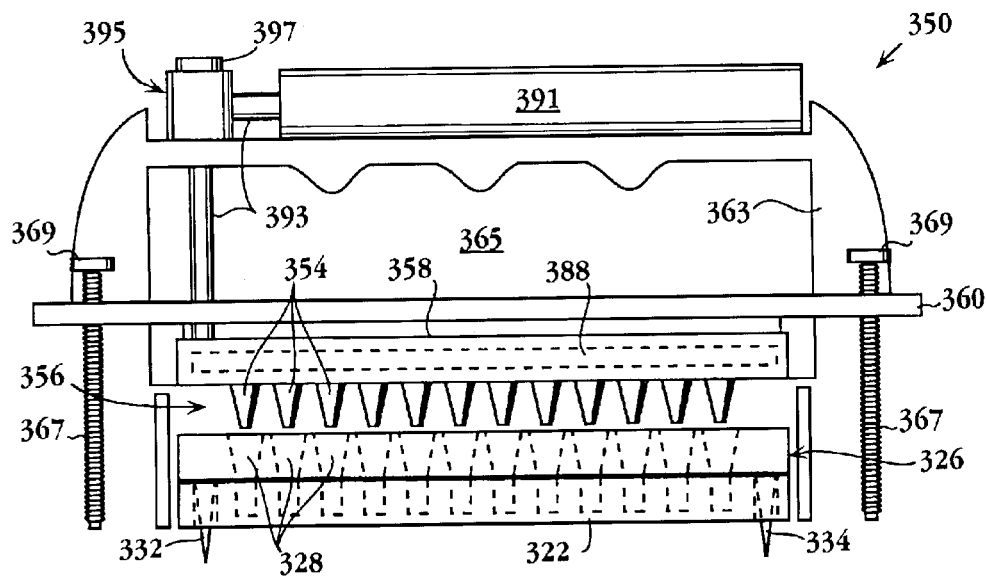
FIG. 17(A) is a side elevational view, with portions shown in phantom, of a hand-operable system for fabricating an array of reagent-carrying beads on a multi-well plate, constructed in accordance with an embodiment of the present invention.
Figure 17B:
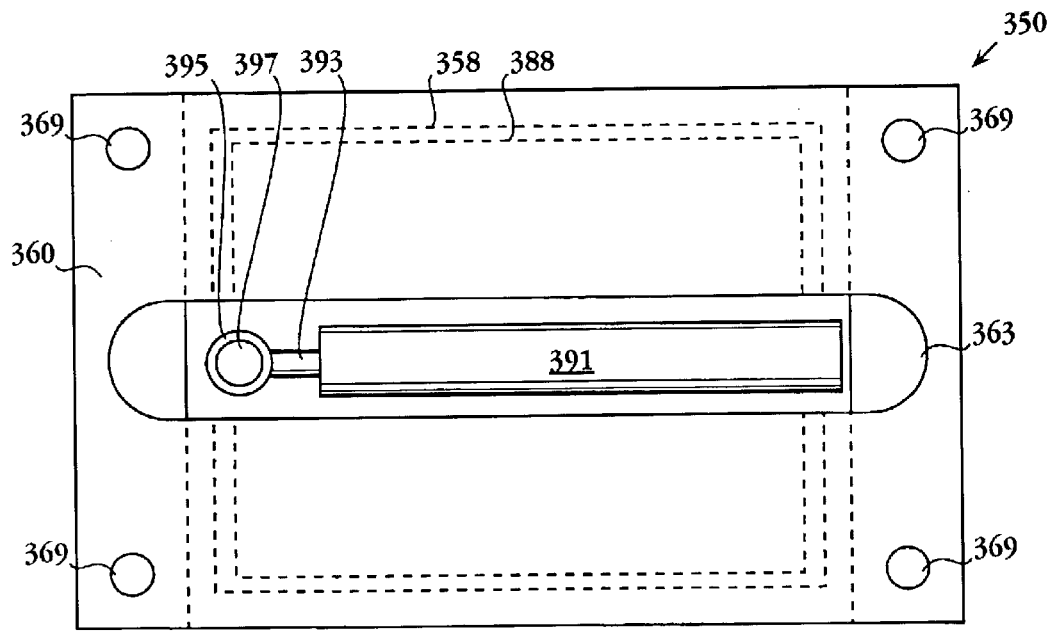
FIG. 17(B) is a top plan view, with portions shown in phantom, of the hand-operable system of FIG. 17(A).

A further aspect of the invention provides a hand-held unit for simultaneously picking up a plurality of reagent-carrying beads and depositing the beads at a desired location. An exemplary arrangement of one such device, denoted generally by the reference numeral 350, is depicted in FIGS. 17(A)–17(B). Here, a rectangular frame member 360, having substantially planar upper and lower broad surfaces, is provided with a handle 363 rigidly attached thereto. Handle 363 is roughly U- or arch-shaped and oriented over frame 360 so as to provide a gap 365 between its central region and the upper surface of frame 360. Preferably, gap 365 is dimensioned to accommodate the fingers of an operator's hand upon grasping handle 363.

A generally rectangular support 358, also having substantially planar upper and lower broad surfaces, is attached to an underside of frame 360. Frame 360 and support 358 are disposed in fixed, spaced relation, with their confronting surfaces generally parallel to one another. A plurality of projections, such as 354, depend from the lower surface of support 358. Preferably, the projections are arranged in an array, such as an 8×12, 16×24, or 32×32 array, although other layouts are possible. Each of the projections has a cavity at a lower end region thereof, adapted to receive a bead, as previously described.

Elongated legs 367, upon which the unit can rest, extend downwardly from respective corner regions of frame 360.

Preferably, the legs are of a type permitting adjustments to the height of the unit. For example, each leg can have threads formed about its outer circumference adapted for mating engagement with internal threads of respective bores formed through the frame's corner regions. A knob, such as 369, can rigidly attach to the upper end of each leg 367 to facilitate manual height adjustments, e.g., by rotating the legs.

Upon grasping handle 363, an operator can pick up the unit 350 and place it over a reagent supply, such as plate 20 of FIG. 1. The reagent-supply locations (wells) of the plate are preferably arranged in an array having a center-to-center spacing substantially like the hand-held unit's projection array 356 so that the two arrays can be aligned. By this construction, each projection 354 of the projection array 356 can be lowered into a respective bead-holding well to attract a reagent bead.

An attraction source is operable at each of the projection end regions in a manner effective to draw individual beads from the supply into respective cavities and to releasably retain them therein. In one embodiment, the attraction source includes a pressure-control assembly capable of generating a reduced pressure (vacuum) at each projection end region. With continued reference to FIGS. 17(A)–17(B), for example, a chamber or manifold 388 can extend through support 358, over the projection array 356. Each projection of the projection array can have an axially extending lumen (not shown) providing fluidic communication between the cavity at its lower end region and the chamber 388 in support 358. In this regard, the projections can be formed, for example, substantially as shown in FIGS. 4(A)–4(B) or FIG. 5. Chamber 388 is further disposed in fluid communication with a pressure-control source. Any suitable pressure control source can be utilized. For example, the pressure control source can be a pump, or a syringe-type device, operable in one mode to evacuate chamber, and in a second mode to pressurize chamber. In one preferred arrangement, shown in FIGS. 17(A)–17(B), the pressure-control source is a resiliently deformable squeeze-type bottle 391 that is mounted to an upper side of handle 363. A connector line 393 permits fluid communication between chamber 388 and bottle 391. Upon deforming or crushing bottle 391 by, for example, a human hand, fluid (e.g., a gas, such as air) can be forced out, thereby effecting a pressure increase in chamber 388 and at each projection end region. When released, bottle 391 substantially returns to its original shape, creating a suction or vacuum force tending to draw air out of chamber 388. The evacuated chamber 388, in turn, generates a reduced pressure at each projection end region. To provide control over the flow of fluid between bottle 391 and chamber 388, a valve assembly, such as at 395, can be situated along flow line 393. Conveniently, a thumb-depressible, spring-biased button 397 located near one end of handle 363, permits manual control (e.g., "on/off") over the flow of fluid through line 393.

Once beads have been attracted to, and retained in, respective cavities of the projection array 356, the beads can be moved to a deposit location and released.

For example, the hand-held unit 350 can be placed over a bead-receiving substrate, such as micro-plate 322 of FIG. 17(A), having a plurality of wells (e.g., 96, 384, 1,024, or more) formed therein. In a preferred embodiment, the wells are arranged with a center-to-center spacing substantially like the projection array 356 so that the two arrays can be aligned. Release of the beads can be accomplished, for example, by discontinuing the retaining force. For some applications, the force of gravity, alone, will be sufficient to cause each bead to fall from a respective cavity down into a respective well. In other applications, it may be desirable to further urge the beads out of the cavities. In this regard, one embodiment contemplates the establishment of an increased pressure in the chamber above the projection array. This can be effected, for example, by pressing upon bottle 391 to further deform (crush) it, thereby forcing some of the remaining air from bottle 391 into chamber 388 and, consequently, down through the lumen of each projection. In this way, the beads can be "blown" out of the cavities down towards the wells.

In one embodiment, the beads are deposited directly into the wells of micro-plate 322. In another embodiment, a conduit assembly, such as 326, is utilized to guide or channel each bead into a respective well. In the exemplary arrangement of FIG. 17(A), conduit assembly 326 includes a plurality of large openings formed along one side, arranged in an array alignable with the projection array 356. A plurality of small openings are formed in the other side of the conduit assembly 326, alignable with the array of wells in micro-plate 322. A generally cone- or funnel-shaped conduit, such as at 328, extends between each large opening and a respective one of the small openings.

Indexing pins, such as 332 and 334, that depend from the lower side of conduit assembly 326, can assist in registering the wells of micro-plate 322 with the lower-opening array of the conduit assembly. Particularly, each indexing pin is alignable with a respective indexing bore formed through a corresponding region of micro-plate 322. Insertion of the indexing pins into the indexing bores substantially aligns the lower-opening array of the conduit assembly with the array of wells of micro-plate.

At this point, it can be well appreciated that the bead dispensing system of the present invention offers a number of advantages over typical liquid dispensing arrangements. For example, the volume of each bead can be accurately determined by measuring it off-line. Also, because beads are solid, they do not drip or splatter, thereby reducing the likelihood of cross-contamination. Further, the bead dispensers of the present invention can be used to dispense multiple reagents without frequent cleaning, and without a substantial risk of clogging. And, because of their high-contrast edges, the presence or absence of a bead at a selected location can be readily determined.

It is also noteworthy that the process of bead dispensing, as taught here, is less energetic than typical fluid ejection systems. For example, ink-jets generally eject fluid at a rate of kilohertz and at a velocity of several meters per second. The present invention, on the other hand, can be used to drop beads into wells at a rate of only one or a few per second. Accordingly, problems associated with very energetic spot deposition, such as splattering, breakage, and misdirected ejection (satellites) can generally be avoided. Notwithstanding the relatively slow rate, as compared to other deposition methods, the system of the present invention is comparatively quite fast owing, among other reasons, to its highly parallel approach.

In another of its aspects, the present invention provides a fluid distributor useful, for example, for depositing a liquid in an array of wells of a micro-plate or card. According to one embodiment, the fluid distributor includes a plurality of elongated conduits disposed in fixed, spaced relation in a common support structure. Each conduit has a large opening at one end and a small opening at its other end. The large openings are disposed in an array along one side of the support structure, and the small openings are disposed in an array along an opposite side of the support structure. A region of each conduit extending from a respective one of the small openings is of capillary size, such that a liquid placed in contact with the small-opening array can be drawn at least partially into the conduits by capillary action. Any inner diameter which effects the desired capillary action can be utilized within the scope of this invention. For example, the capillary-size regions can be formed with an inner diameter of less than about 1 mm. To further encourage the desired capillary action, the capillary-size region of each conduit can be provided with inner sidewalls that are hydrophilic.

Figure 18:
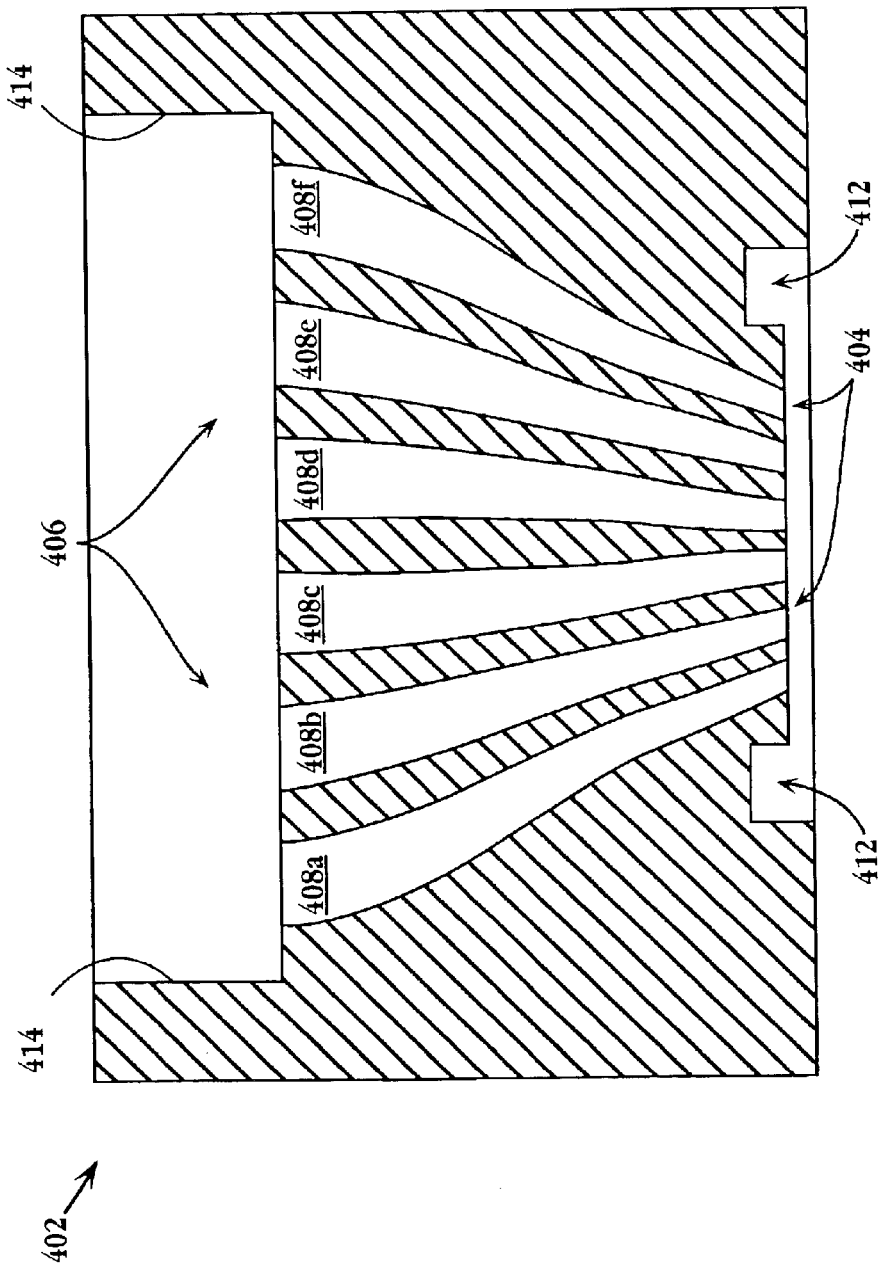
FIG. 18 is a side cross-sectional view of a fluid distributor having an array of conduits for transferring a liquid from a vessel to an array of wells of a micro-plate or card, according to an embodiment of the present invention.
Figure 19A:
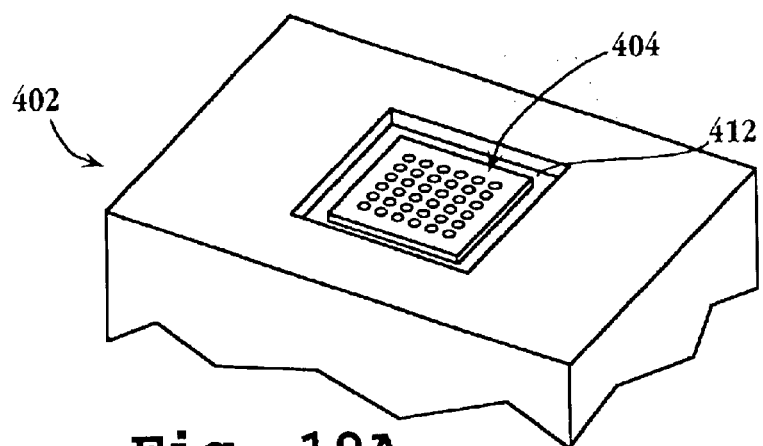
FIG. 19(A) is a perspective view showing an array of small openings, surrounded by a channel, formed in one side of the fluid distributor of FIG. 18.
Figure 19B:
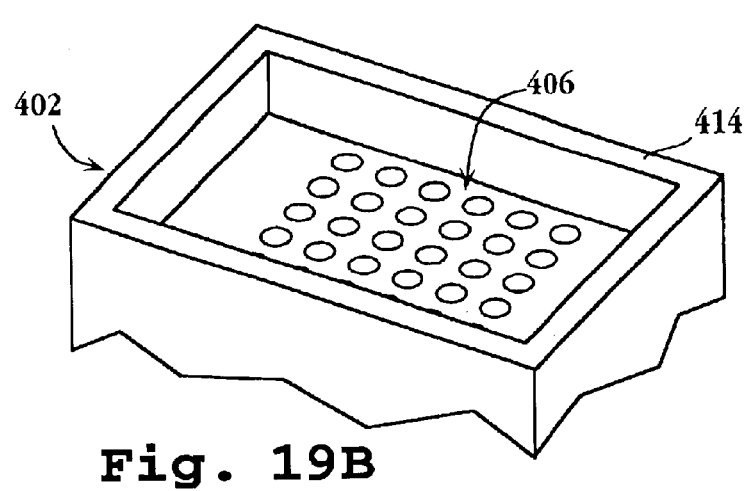
FIG. 19(B) is a perspective view showing an array of large openings, surrounded by an upstanding peripheral wall, formed on one side of the fluid distributor of FIG. 18.

With reference to FIGS. 18 and 19(A)–19(B), an exemplary fluid distributor 402 is shown. An array of small openings, as at 404, are provided on one side of distributor 402 and an array of large openings, as at 406, are provided on an opposite side. The two arrays of openings can be arranged with a like pitch, or they can differ from one another. In the illustrated arrangement, small-opening array 404 is arranged with a substantially reduced pitch as compared to large-opening array 406. A conduit extends between each large opening and a respective one of the small openings. FIG. 18 shows conduits 408a–408f, each having sidewalls that taper (i.e., decrease in diameter) along the direction from a respective large opening to a small opening. As shown in FIGS. 18 and 19(A), a groove or channel 412 extends around the small-opening array 404. And as shown in FIGS. 18 and 19(B), an upstanding peripheral wall 414 extends around the large-opening array 406 on the opposite side of the distributor 402.

Figure 21B:
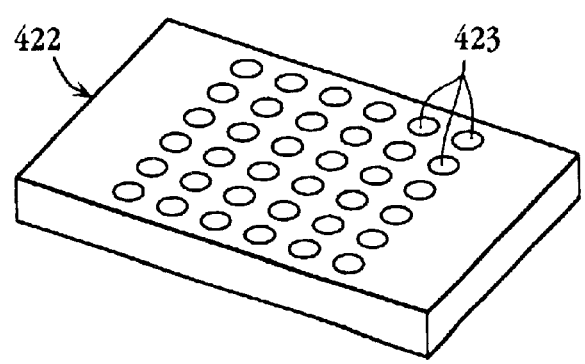
FIG. 21(B) is a perspective view of the multi-well plate shown under the fluid distributor in FIG. 21(A).
Figure 20:
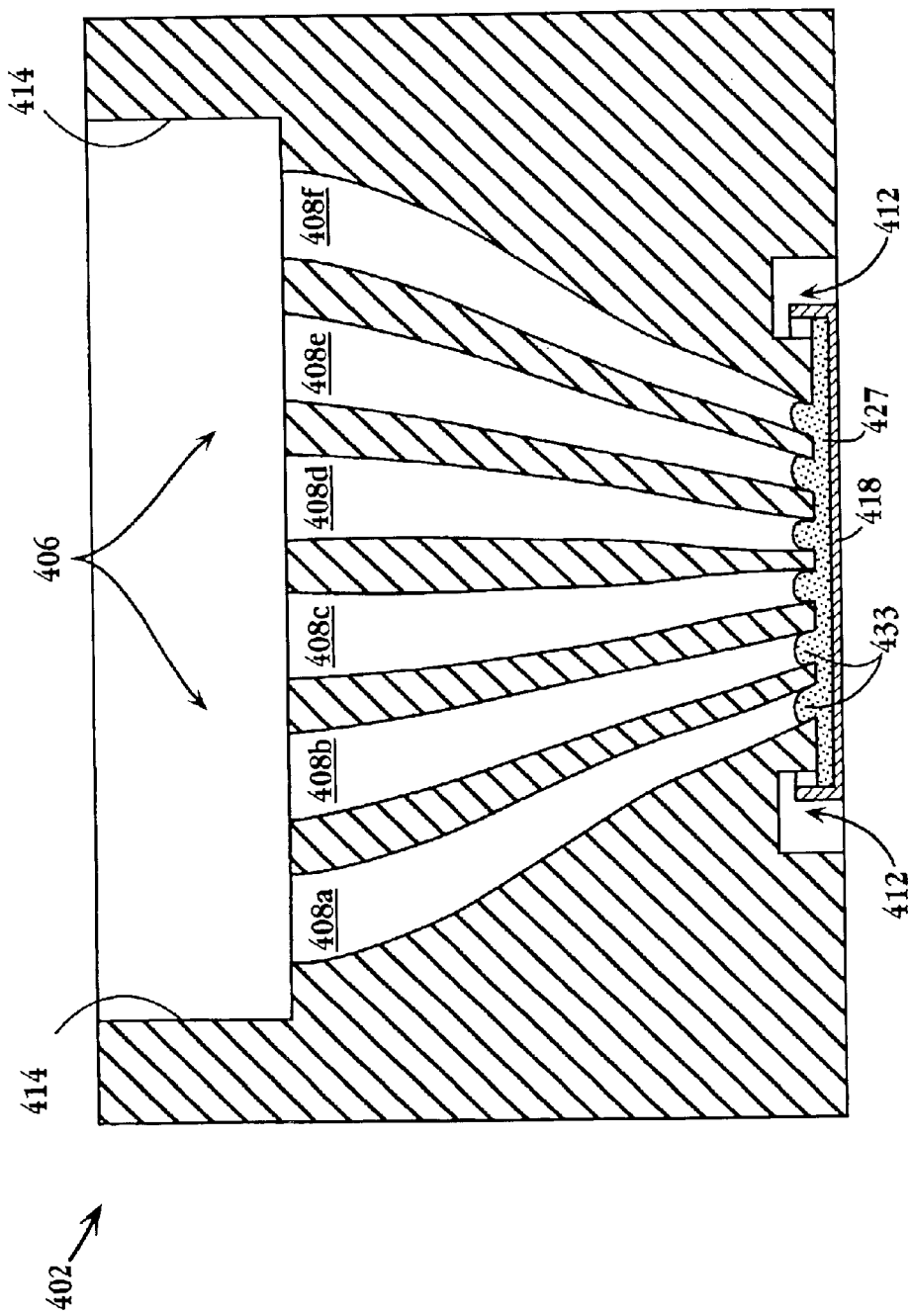
FIG. 20 is a side cross-sectional view of the fluid distributor of FIGS. 18–19 disposed over a vessel containing a liquid, and showing portions of the liquid drawn partially into the conduits of the fluid distributor by capillary action, in accordance with the teachings of the present invention.
Figure 21A:
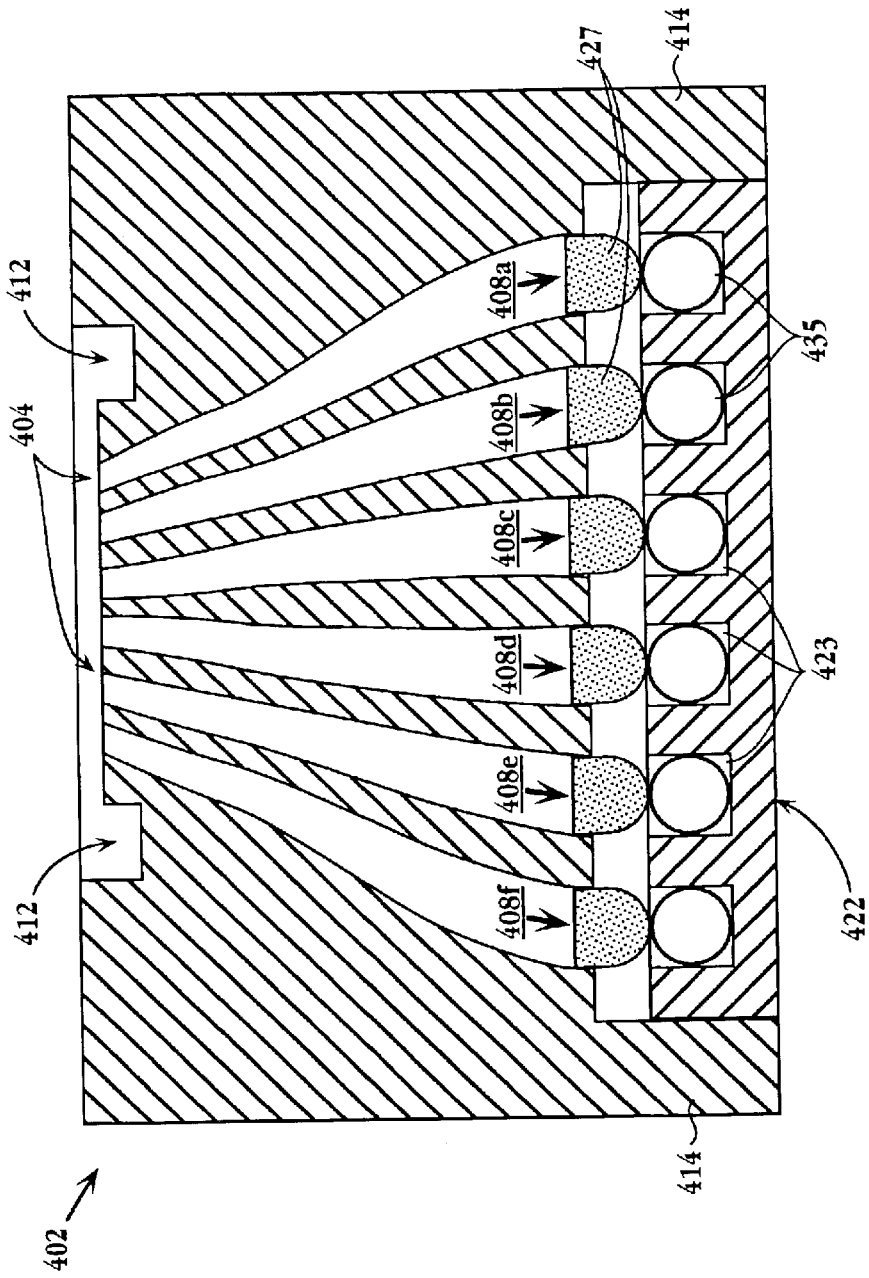
FIG. 21(A) is a side cross-sectional view of the fluid distributor of FIGS. 18–20 inverted over a multi-well plate, showing aliquots of liquid that have traveled downward through respective conduits to form drops at each of the large openings, over respective bead-containing wells of the plate.
Figure 22:
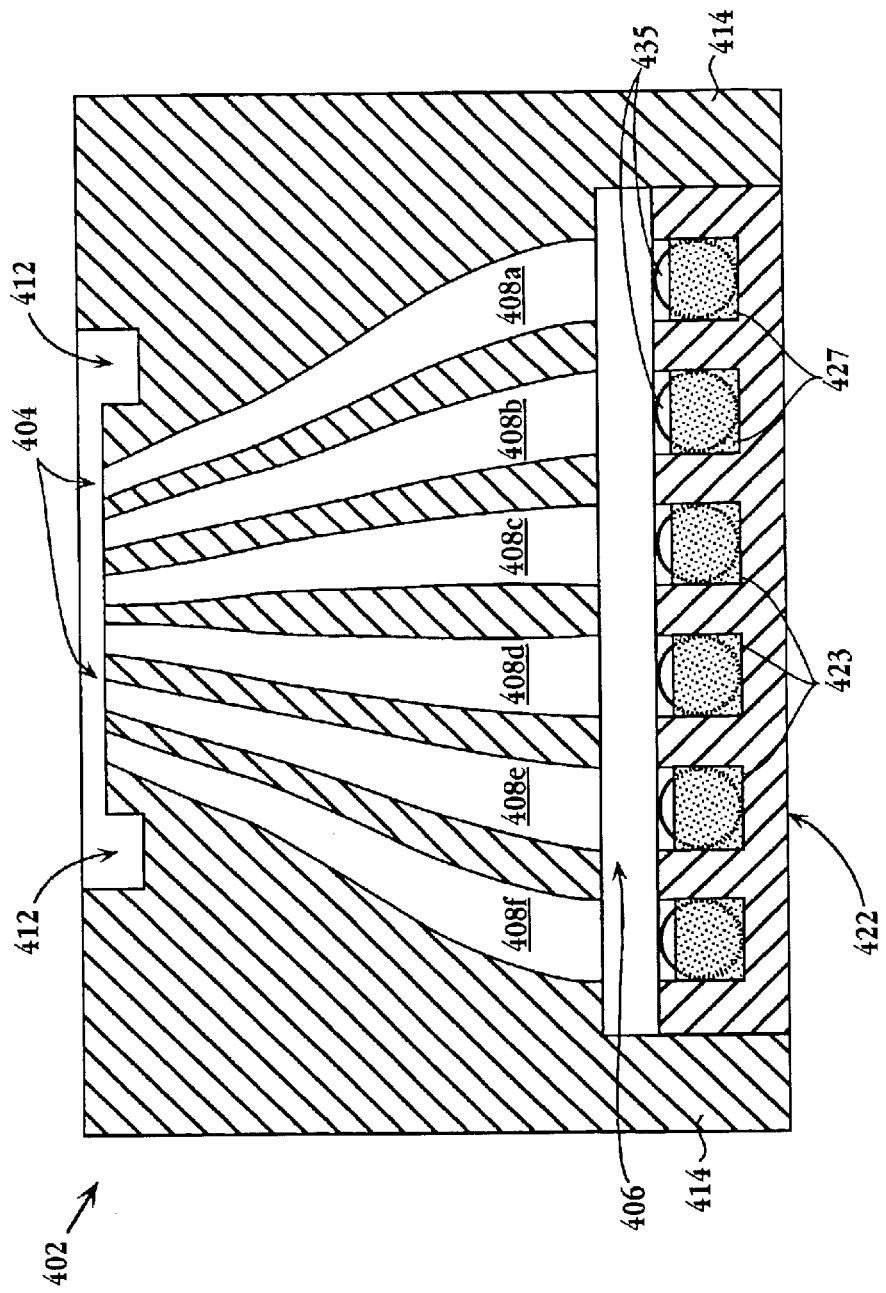
FIG. 22 is a side cross-sectional view of the inverted fluid distributor of FIG. 21(A), with the drops having been pulled into the wells of the multi-well plate due to adhesive forces with the beads.

With additional reference to FIG. 20, a vessel 418 is provided for holding a selected fluid, as at 427. Vessel 418 is provided with a bottom, sidewalls, and an open top. The sidewalls of vessel 418 are configured to register with channel 412 about the small-opening array 404 so that each small opening can be placed in contact with the fluid 427. The small openings, and a region of their respective conduits, are sized such that capillary action can draw some of the fluid into each conduit, as at 433 in FIG. 20. The amount of fluid drawn into each conduit will depend upon the nature of the fluid, the material composition of the conduit, and the diameter of each opening and section of conduit thereabove. This amount can be determined experimentally and/or calculated using principles well known to those skilled in the art. Upon lifting the fluid distributor from the vessel, the drawn-in fluid will remain inside the conduits. The fluid distributor 402 can then be turned over and placed over a substrate, such as multi-well plate 422 shown in FIGS. 21(A)–21(B) and FIG. 22. It should be noted that the wells 423 of plate 422 are disposed in an array alignable with the large-opening array 406 of the fluid distributor 402. Fluid 427 can then be permitted to flow from the small-opening end to the large-opening end of each conduit, eventually forming a meniscus at each end of the inverted large-opening array, as illustrated in FIG. 21(A). Upon contacting an object adjacent each large opening, such as a reagent bead 435, adhesive forces between the liquid and the object can pull the fluid out of the tubes and into the wells, as illustrated in FIG. 22.

It should be noted that vessel 418 can hold any desired fluid. For example, the fluid deposited in the bead-containing wells can be a solvent capable of dissolving and/or swelling a coating material enveloping each bead 435, thereby providing access to a reagent core.

Also, it should be appreciated that certain disadvantages often associated with the deposition of a liquid into a well already holding a liquid, such as cross-contamination due to splashing, can be avoided using the fluid distributor of the present invention, wherein a liquid is touched to a bead in each well.

Those skilled in the art can now appreciate from the foregoing description that the broad teachings of the present invention can be implemented in a variety of forms. Therefore, while this invention has been described in connection with particular embodiments and examples thereof, the true scope of the invention should not be so limited. Various changes and modification may be made without departing from the scope of the invention, as defined by the appended claims.

What is claimed is:

1. A system for picking up a plurality of submillimeter beads from a bead supply and transferring said beads to a desired location, comprising:
   a plurality of projections depending from a support at spaced-apart locations defining an array;
   a cavity formed at a lower end region of each of said projections, each of said cavities defined by (i) a lower opening, (ii) an upper ceiling region, and (iii) a sidewall extending between said lower opening and said upper ceiling region;
   wherein said upper ceiling region defines a surface extending inwardly from said sidewall;
   wherein each cavity has a substantially constant diameter along a region extending between its lower opening and its upper ceiling region, such that lines extending longitudinally along confronting inner surfaces of each sidewall are substantially parallel to one another; and
   an attraction source, operable at said projection end regions, effective to draw beads from said supply into said cavities and to releasably retain said beads therein.

2. The system of claim 1, wherein at least a lower portion of said sidewall of each projection comprises a resiliently flexible material, such that said flexible lower portion of said sidewall can bend while maintaining the shape of said cavity so that said lower opening can bend to face said beads in said bead supply.

3. The system of claim 1, wherein the diameter of said lower opening is between about 100–1,250 micrometers and the longitudinal length of said sidewall, from said lower opening and to said upper ceiling, is between about 0.50–1.25 times the diameter of said lower opening.

4. The system of claim 1, wherein the diameter of said lower opening is between about 250–750 micrometers and the longitudinal length of said sidewall, from said lower opening and to said upper ceiling, is between about 0.75–1.10 times the diameter of said lower opening.

5. The system of claim 1, wherein said cavity is dimensioned to receive at least half of one submillimeter bead, and to preclude entry therein of a substantial portion of a second such bead.

6. The system of claim 2, wherein said resiliently flexible sidewall has a generally cylindrical shape, with both an inner diameter and a longitudinal depth of between about 100–1,250 micrometers.

7. The system of claim 6, wherein said inner diameter and longitudinal depth are between about 350–425 micrometers.

8. The system of claim 1, wherein said cavity is formed by a resiliently flexible, tubular sleeve fit over the end of a respective projection, said sleeve having an overhang region extending below a terminal end of said projection defining said sidewall; and wherein said terminal end of said projection, facing said cavity, defines said upper ceiling region of said cavity.

9. A system for picking up a plurality of submillimeter beads from a bead supply and transferring said beads to a desired location, comprising:

a plurality of projections depending from a support at spaced-apart locations defining an array;

a cavity formed at a lower end region of each of said projections, each of said cavities defined by (i) a lower opening, (ii) an upper ceiling region, and (iii) a sidewall extending between said lower opening and said upper ceiling region;

wherein said upper ceiling region defines a surface extending inwardly from said sidewall;

an attraction source, operable at said projection end regions, effective to draw beads from said supply into said cavities and to releasably retain said beads therein;

a plurality of ampules for containing said bead supply, said ampules disposed in an array alignable with said projection array; and a plurality of covers, each cover configured to extend over an upper opening of one of said ampules.

10. The system of claim 9, wherein each of said covers is a frangible membrane.

11. The system of claim 9, wherein said support is held by a frame that is
(i) adapted to pivot about a generally vertical axis, rendering movable said projection array along a generally arcuate or circular pathway, and
(ii) adapted for reciprocal linear motion along a generally vertical pathway;
such movement permitting said projections to be aligned with said ampule array and lowered so that each projection can enter a respective one of said ampules.

12. The system of claim 9, wherein one of said ampules holds a plurality of submillimeter beads that carry a first set of analyte-specific reagents, and another of said ampules holds a plurality of submillimeter beads that carry a second set of analyte-specific reagents; said first and second reagent sets differing from each other by at least one analyte-specific component.

13. A system for picking up a plurality of submillimeter beads from a bead supply and transferring said beads to a desired location, comprising:

a plurality of projections depending from a support at spaced-apart locations defining an array;

a cavity formed at a lower end region of each of said projections, each of said cavities defined by (i) a lower opening, (ii) an upper ceiling region, and (iii) a sidewall extending between said lower opening and said upper ceiling region;

wherein said upper ceiling region defines a surface extending inwardly from said sidewall; and an attraction source, operable at said projection end regions, effective to draw beads from said supply into said cavities and to releasably retain said beads therein;

wherein each of said projections is a capillary tube having an axial lumen extending therethrough, each lumen having (i) a first end that opens into a respective one of said cavities through said ceiling region, and (ii) a second end disposed in fluid communication with a pressure-control assembly;

wherein said pressure-control assembly includes (i) a vacuum pump operable to establish a reduced pressure within each of said lumens, said reduced pressure defining said attraction source; and (ii) a pump operable to establish an increased pressure within each of said lumens, said increased pressure effective to displace any beads retained in said cavities.

14. The system of claim 13, wherein each of said lumens has an inner diameter at said first end that is smaller than the diameter of a respective cavity at a location directly adjacent said ceiling region.

15. The system of claim 14, wherein each of said cavities has an inner diameter at a location directly adjacent said ceiling region of greater than 275 micrometers, and each of said lumens has an inner diameter at said first end of between 100–275 micrometers.

16. A system for picking up a plurality of submillimeter beads from a bead supply and transferring said beads to a desired location, comprising:

a plurality of projections depending from a support at spaced-apart locations defining an array;

a cavity formed at a lower end region of each of said projections, each of said cavities defined by (i) a lower opening, (ii) an upper ceiling region, and (iii) a sidewall extending between said lower opening and said upper ceiling region;

wherein said upper ceiling region defines a surface extending inwardly from said sidewall;

an attraction source, operable at said projection end regions, effective to draw beads from said supply into said cavities and to releasably retain said beads therein; and a detection system having a field of view extending along each of said projection end regions, and adapted to sense the presence or absence of a bead retained in said cavities;

wherein said detection system includes a plurality of elongated light-conductive fibers, each fiber having one end that extends along one of said projections and faces said cavity, and a second end disposed in optical communication with a camera device.

17. A system for picking up a plurality of submillimeter beads from a bead supply and transferring said beads to a desired location, comprising:

a plurality of projections depending from a support at spaced-apart locations defining an array;

a cavity formed at a lower end region of each of said projections, each of said cavities defined by (i) a lower opening, (ii) an upper ceiling region, and (iii) a sidewall extending between said lower opening and said upper ceiling region;

wherein said upper ceiling region defines a surface extending inwardly from said sidewall;

an attraction source, operable at said projection end regions, effective to draw beads from said supply into said cavities and to releasably retain said beads therein; and a conduit assembly having a plurality of conduits for separately channeling a plurality of submillimeter beads released from said cavities to desired locations on a substrate, said conduits having (i) first openings at their upper ends disposed in an array having a center-to-center pitch like that of the projection array such that the first openings are substantially alienable under the projections, and (ii) second openings at their lower ends disposed in an array having a center-to-center pitch like that of the substrate array such that the second openings are substantially aligned thereover;

wherein said second openings are disposed in an array having a center-to-center pitch substantially smaller than that of the first-opening array.

18. The system of claim 16, wherein the center-to-center pitch of the second-opening array is reduced by a factor of at least about 3, as compared to that of the first-opening array.

19. The system of claim 16, further comprising a substrate, wherein said substrate is a micro-card having a plurality of wells disposed in an array alignable under said second-opening array.

20. The system of claim 18, further comprising
a detection system having a field of view extending into each of said conduits, and adapted to sense the presence or absence of a bead in each well of said microcard.

21. A system for picking up a plurality of submillimeter beads from a bead supply and transferring said beads to a desired location, comprising:
a plurality of projections depending from a support at spaced-apart locations defining an array;
a cavity formed at a lower end region of each of said projections, each of said cavities defined by (i) a lower opening, (ii) an upper ceiling region, and (iii) a sidewall extending between said lower opening and said upper ceiling region;
wherein said upper ceiling region defines a surface extending inwardly from said sidewall;
an attraction source, operable at said projection end regions, effective to draw beads from said supply into said cavities and to releasably retain said beads therein; and
a detection system having a field of view extending along each of said projection end regions, and adapted to sense the presence or absence of a bead retained in said cavities;
wherein said detection system includes at least one image capture device positioned to capture and display an image that includes the lower end region of each of said projections to provide an indication of the presence or absence of a bead retained in the lower end region cavity of each projection.

22. The system of claim 20, wherein said detection system includes a pair of image capture devices.

23. The system of claim 20, wherein the captured and displayed image further provides an indication of whether more than one bead is retained in the lower end region cavity of any projection.

24. A system for picking up a plurality of submillimeter beads from a bead supply and transferring said beads to a desired location, comprising:
a plurality of projections depending from a support at spaced-apart locations defining an array;
a cavity formed at a lower end region of each of said projections, each of said cavities defined by (i) a lower opening, (ii) an upper ceiling region, and (iii) a sidewall extending between said lower opening and said upper ceiling region;
wherein said upper ceiling region defines a surface extending inwardly from said sidewall;
an attraction source, operable at said projection end regions, effective to draw beads from said supply into said cavities and to releasably retain said beads therein; and
a conduit assembly having a plurality of conduits for separately channeling a plurality of submillimeter beads released from said cavities to desired locations on a substrate, said conduits having (i) first openings at their upper ends disposed in an array having a center-to-center pitch like that of the projection array such that the first openings are substantially alignable under the projections, and (ii) second openings at their lower ends disposed in an array having a center-to-center pitch like that of the substrate array such that the second openings are substantially aligned thereover;
wherein each of said conduits is curved along a longitudinal direction from said first opening to said second opening.

25. A system for picking up a plurality of submillimeter beads from a bead supply and transferring said beads to a desired location, comprising:
a plurality of projections depending from a support at spaced-apart locations defining an array;
a cavity formed at a lower end region of each of said projections, each of said cavities defined by (i) a lower opening, (ii) an upper ceiling region, and (iii) a sidewall extending between said lower opening and said upper ceiling region;
wherein said upper ceiling region defines a surface extending inwardly from said sidewall;
an attraction source, operable at said projection end regions, effective to draw beads from said supply into said cavities and to releasably retain said beads therein;
a conduit assembly having a plurality of conduits for separately channeling a plurality of submillimeter beads released from said cavities to desired locations on a substrate, said conduits having (i) first openings at their upper ends disposed in an array having a center-to-center pitch like that of the projection array such that the first openings are substantially alienable under the projections, and (ii) second openings at their lower ends disposed in an array having a center-to-center pitch like that of the substrate array such that the second openings are substantially aligned thereover; and
a parallelogram linkage assembly supporting said conduit assembly for reciprocal arcuate movement between a raised position and a lowered position.

26. The system of claim 24, further comprising:
(i) a carousel adapted for rotation about a central axis, said carousel (a) pivotally supporting said parallelogram linkage assembly for movement radially about a central axis of rotation of the carousel, and (b) having a substrate holding area adjacent to said parallelogram linkage assembly; and
(ii) a stationary rail extending along an inner region of said carousel and having a continuous bearing surface in mechanical communication with said parallelogram linkage assembly, said bearing surface having (a) a region disposed a first distance from central axis and at a first vertical height, whereat said conduit array assumes said lowered position over said substrate holding area, and (b) a region disposed a second distance from said central axis, shorter than said first distance, and at a second vertical height, higher than said vertical height, whereat said conduit array assumes said raised position.

27. A system for picking up a plurality of submillimeter beads from a bead supply and transferring said beads to a desired location, comprising:
a plurality of projections depending from a support at spaced-apart locations defining an array;
a cavity formed at a lower end region of each of said projections, each of said cavities defined by (i) a lower opening, (ii) an upper ceiling region, and (iii) a sidewall extending between said lower opening and said upper ceiling region;
wherein said upper ceiling region defines a surface extending inwardly from said sidewall;
an attraction source, operable at said projection end regions, effective to draw beads from said supply into said cavities and to releasably retain said beads therein; and
a conduit assemble having a plurality of conduits for separately channeling a plurality of submillimeter beads released from said cavities to desired locations on a substrate, said conduits having (i) first openings at their upper ends disposed in an array having a center-to-center center pitch like that of the projection array such that the first openings are substantially alignable under the projections, and (ii) second openings at their lower ends disposed in an array having a center-to-center pitch like that of the substrate array such that the second openings are substantially aligned thereover; and a substrate, wherein said substrate is provided with a pair of spaced-apart indexing holes, each being aligned with a respective indexing pin depending from a lower side of said conduit array; whereupon registering said indexing pins in said indexing holes substantially aligns said second-opening array with said well array of said substrate.

28. A system for picking up a plurality of submillimeter beads from a bead supply and transferring said beads to a desired location, comprising:

a plurality of projections depending from a support at spaced-apart locations defining an array;

a cavity formed at a lower end region of each of said projections, each of said cavities defined by (i) a lower opening, (ii) an upper ceiling region, and (iii) a sidewall extending between said lower opening and said upper ceiling region;

wherein said upper ceiling region defines a surface extending inwardly from said sidewall;

an attraction source, operable at said projection end regions, effective to draw beads from said supply into said cavities and to releasably retain said beads therein;

a conduit assembly having a plurality of conduits for separately channeling a plurality of submillimeter beads released from said cavities to desired locations on a substrate, said conduits having (i) first openings at their upper ends disposed in an array having a center-to-center pitch like that of the projection array such that the first openings are substantially alignable under the projections, and (ii) second openings at their lower ends disposed in an array having a center-to-center pitch like that of the substrate array such that the second openings are substantially aligned thereover;

a detection system having a field of view extending into each of said conduits, and adapted to sense the presence or absence of a bead on said substrate under each of said second openings;

wherein said detection system further comprises:

a radiation source adapted to illuminate said substrate at locations below each of said second openings; and a plurality of elongated light-conductive fibers, each fiber having (i) one end disposed to receive light traveling up through a respective conduit, and (ii) a second end that communicates with a camera device.

29. A system for picking up a plurality of submillimeter beads from a bead supply and transferring said beads to a desired location, comprising:

a plurality of projections depending from a support at spaced-apart locations defining an array;

a cavity formed at a lower end region of each of said projections, each of said cavities defined by (i) a lower opening, (ii) an upper ceiling region, and (iii) a sidewall extending between said lower opening and said upper ceiling region;

wherein said upper ceiling region defines a surface extending inwardly from said sidewall;

an attraction source, operable at said projection end regions, effective to draw beads from said supply into said cavities and to releasably retain said beads therein;

a conduit assembly having a plurality of conduits for separately channeling a plurality of submillimeter beads released from said cavities to desired locations on a substrate, said conduits having (i) first openings at their upper ends disposed in an array having a center-to-center pitch like that of the projection away such that the first openings are substantially alignable under the projections, and (ii) second openings at their lower ends disposed in an array having a center-to-center pitch like that of the substrate array such that the second openings are substantially aligned thereover; and a support structure, wherein said first openings are disposed in an array along one side of said support structure, and said second openings are disposed in an array along an opposite side of said support structure, wherein said first-opening array is arranged with a center-to-center pitch larger than that of said second-opening array, and wherein a region of each conduit extending from a respective one of said second openings is of capillary size, such that a liquid placed in contact with said second-opening array can be drawn at least partially into said conduits by way of capillary action.

30. The system of claim 28, wherein said capillary-size region of each conduit has an inner diameter of less than about 1 mm.

31. The system of claim 28, wherein capillary-size region of each conduit has inner sidewalls that are hydrophilic.

32. A system for picking up a plurality of submillimeter beads from a bead supply and transferring said beads to a desired location, comprising:

a plurality of projections depending from a support at spaced-apart locations defining an array;

a cavity formed at a lower end region of each of said projections, each of said cavities defined by (i) a lower opening, (ii) an upper ceiling region, and (iii) a sidewall extending between said lower opening and said upper ceiling region;

wherein said upper ceiling region defines a surface extending inwardly from said sidewall;

an attraction source, operable at said projection end regions, effective to draw beads from said supply into said cavities and to releasably retain said beads therein;

a covering system for covering said beads after said beads have been disposed at said desired locations on a substrate, wherein said desired locations comprise an array of wells formed in said substrate, said covering system comprising:

a continuous web of a cover material mounted for movement from a supply position to a take-up position; and a shearing blade mounted for reciprocal linear motion along a direction substantially normal to said web for cutting a portion of said cover material at a region between said supply position and said take-up position.

33. The system of claim 31, wherein said cover system further comprises:

an idler reel for holding said cover material in said supply position;

a driven reel for taking up said cover material in said take-up position;

a movable piston for effecting said linear reciprocal motion, said movable piston having a lower face on which said movable blade is mounted; and a resiliently compliant, substantially planar surface provided on said lower face along a region between said movable blade for pressing said cover material against an upper surface of said substrate.

34. The system of claim 31, wherein said cover material comprises an optically clear film.

* * * * *